(12) United States Patent
Mozzicato et al.

(10) Patent No.: US 11,963,836 B2
(45) Date of Patent: *Apr. 23, 2024

(54) DETACHABLE RECYCLING CONTAINER

(71) Applicant: Solmetex LLC, Northborough, MA (US)

(72) Inventors: Nicholas Mozzicato, Acton, MA (US); Richard Goulston, Stuart, FL (US); Robin Schofield, Lancaster, MA (US); Michael Toole, Norton, MA (US)

(73) Assignee: Solmetex LLC, Northborough, MA (US)

( * ) Notice: Subject to any disclaimer, the term of this patent is extended or adjusted under 35 U.S.C. 154(b) by 881 days.

This patent is subject to a terminal disclaimer.

(21) Appl. No.: 16/941,522

(22) Filed: Jul. 28, 2020

(65) Prior Publication Data

US 2021/0106412 A1 Apr. 15, 2021
US 2024/0000554 A9 Jan. 4, 2024

Related U.S. Application Data

(63) Continuation-in-part of application No. 16/033,823, filed on Jul. 12, 2018, now Pat. No. 10,779,923, which is a continuation-in-part of application No. 15/730,828, filed on Oct. 12, 2017, now Pat. No. 10,646,313.

(60) Provisional application No. 62/414,712, filed on Oct. 29, 2016, provisional application No. 62/406,990, filed on Oct. 12, 2016.

(51) Int. Cl.
*A61C 17/06* (2006.01)
*A61M 1/00* (2006.01)
*B01D 21/24* (2006.01)
*B65D 43/02* (2006.01)

(52) U.S. Cl.
CPC ............ *A61C 17/065* (2019.05); *A61M 1/88* (2021.05); *B01D 21/2444* (2013.01); *B65D 43/0231* (2013.01); *A61M 1/60* (2021.05); *A61M 1/79* (2021.05); *B65D 2543/00092* (2013.01)

(58) Field of Classification Search
CPC .... A61C 17/065; A61M 1/64; B65D 43/0231; B65D 2543/00092; B01D 21/2444
See application file for complete search history.

(56) References Cited

U.S. PATENT DOCUMENTS

| | | |
|---|---|---|
| 54,414 A | 5/1866 | Sangster |
| D24,111 S | 3/1895 | Landgraf |
| 1,032,879 A | 7/1912 | Carlton |

(Continued)

FOREIGN PATENT DOCUMENTS

| | | |
|---|---|---|
| CA | 2442513 A1 | 3/2005 |
| EP | 1366728 A1 | 12/2003 |

(Continued)

OTHER PUBLICATIONS

"International Standard ISO 11143: Dentistry—Amalgam separators"; Second edition; ISO Copyright Office, Switzerland; Jul. 1, 2008; (32 pages).

(Continued)

*Primary Examiner* — Nicholas D Lucchesi

(57) ABSTRACT

The present invention provides dental amalgam recycling systems, useful for recycling particles from a dental liquid effluent drawn, for example, from a suctioning device.

21 Claims, 26 Drawing Sheets

(56) References Cited

U.S. PATENT DOCUMENTS

| | | |
|---|---|---|
| 2,467,547 A | 4/1949 | Birnbaum |
| D189,743 S | 2/1961 | Happe |
| 3,665,682 A | 5/1972 | Ciavattoni |
| 3,870,486 A | 3/1975 | Eriksson |
| 3,988,134 A | 10/1976 | Gandrud |
| 4,083,705 A | 4/1978 | Parise |
| 4,097,381 A | 6/1978 | Ritzler |
| 4,226,054 A | 10/1980 | Coty |
| 4,326,952 A | 4/1982 | Blake |
| 4,385,891 A | 5/1983 | Ligotti |
| 4,599,170 A | 7/1986 | Friedman |
| D286,268 S | 10/1986 | Wolff |
| D288,528 S | 3/1987 | Parad |
| D288,529 S | 3/1987 | Parad |
| 4,753,632 A | 6/1988 | Hofmann |
| 4,761,235 A | 8/1988 | Haentjens |
| D306,266 S | 2/1990 | Hargrove |
| D306,649 S | 3/1990 | Lapicola |
| 4,911,315 A | 3/1990 | Shrum |
| 4,934,545 A | 6/1990 | Pezzoli |
| 4,951,845 A | 8/1990 | Pezzoli |
| 4,957,621 A | 9/1990 | Rohloff |
| 5,018,971 A | 5/1991 | Trawoeger |
| 5,114,578 A | 5/1992 | Sundstrom |
| 5,125,522 A | 6/1992 | Pezzoli |
| D341,085 S | 11/1993 | Charbonneau |
| 5,330,641 A | 7/1994 | Cattani |
| D349,647 S | 8/1994 | Moffitt |
| 5,343,592 A | 9/1994 | Parise |
| D359,236 S | 6/1995 | Spafford |
| 5,421,996 A | 6/1995 | Trawoeger |
| 5,484,282 A | 1/1996 | Trawoger |
| 5,509,551 A | 4/1996 | Terrell, II |
| D372,426 S | 8/1996 | Garnett |
| D374,481 S | 10/1996 | McCallister |
| 5,613,851 A | 3/1997 | Trawoeger |
| D384,280 S | 9/1997 | Kuczer |
| 5,730,322 A | 3/1998 | Iba |
| 5,741,134 A | 4/1998 | Davis |
| 5,743,735 A | 4/1998 | Vollstedt |
| 5,795,159 A | 8/1998 | Ralls |
| 5,797,742 A | 8/1998 | Fraker |
| 5,873,494 A | 2/1999 | Dallas, Jr. |
| 5,958,113 A | 9/1999 | Collins |
| D423,354 S | 4/2000 | Lin |
| 6,083,307 A | 7/2000 | Dular |
| D428,768 S | 8/2000 | Betras |
| D431,158 S | 9/2000 | Schwab |
| D433,275 S | 11/2000 | Betras |
| 6,149,812 A | 11/2000 | Erickson |
| D435,194 S | 12/2000 | Betras |
| 6,409,803 B1 | 6/2002 | Tremel |
| 6,521,131 B1 | 2/2003 | Hamilton |
| 6,592,754 B2 | 7/2003 | Chilibeck |
| 6,592,769 B1 | 7/2003 | Erickson |
| 6,638,066 B2 | 10/2003 | Hubner |
| 6,660,160 B1 | 12/2003 | Ernryd |
| 6,692,636 B2 | 2/2004 | Chilibeck |
| 6,790,038 B2 | 9/2004 | Hubner |
| 6,797,178 B2 | 9/2004 | Albiston |
| D503,097 S | 3/2005 | Burr |
| D503,110 S | 3/2005 | Burr |
| 6,946,069 B2 | 9/2005 | Chilibeck |
| D522,359 S | 6/2006 | Van Diepen |
| 7,063,793 B2 | 6/2006 | Albiston |
| 7,080,425 B2 | 7/2006 | Smith |
| 7,131,839 B2 | 11/2006 | March |
| 7,156,214 B2 | 1/2007 | Pradel |
| 7,166,214 B2 | 1/2007 | Armstrong |
| D536,247 S | 2/2007 | Burr |
| 7,182,599 B2 | 2/2007 | Stone |
| 7,306,460 B2 | 12/2007 | Hubner |
| D574,237 S | 8/2008 | Yates, III |
| 7,422,615 B2 | 9/2008 | Kim |
| 7,604,674 B2 | 10/2009 | Han |
| 7,753,976 B2 | 7/2010 | Hyun |
| 7,767,079 B2 | 8/2010 | Darcy |
| D630,094 S | 1/2011 | Maxwell |
| 8,393,898 B2 | 3/2013 | McCary |
| 8,636,837 B2 | 1/2014 | Nonnenmacher |
| 8,692,636 B2 | 4/2014 | Reuber |
| D705,059 S | 5/2014 | Hutchinson |
| D706,135 S | 6/2014 | Hutchinson |
| D727,149 S | 4/2015 | Humm |
| D750,962 S | 3/2016 | Liu |
| 9,332,969 B2 | 5/2016 | Han |
| D835,264 S | 12/2018 | Mozzicato |
| D835,778 S | 12/2018 | Mozzicato |
| D835,779 S | 12/2018 | Mozzicato |
| D840,533 S | 2/2019 | Mozzicato |
| D840,534 S | 2/2019 | Mozzicato |
| D848,612 S | 5/2019 | Mozzicato |
| 10,342,647 B2 | 7/2019 | Stolarik |
| 10,646,313 B2 | 5/2020 | Mozzicato |
| 10,779,923 B2 | 9/2020 | Mozzicato |
| 11,278,382 B2 | 3/2022 | Stolarik |
| 2001/0047956 A1 | 12/2001 | Albiston |
| 2002/0185186 A1 | 12/2002 | Juliar |
| 2003/0003417 A1 | 1/2003 | Hubner |
| 2004/0259052 A1 | 12/2004 | Hubner |
| 2005/0016913 A1 | 1/2005 | Giesel |
| 2005/0282107 A1* | 12/2005 | Stone .................. A61C 17/065 433/92 |
| 2006/0065594 A1 | 3/2006 | Armstrong |
| 2006/0093990 A1* | 5/2006 | Stone ..................... A61C 17/06 433/92 |
| 2010/0264074 A1 | 10/2010 | Darcy |
| 2013/0199975 A1* | 8/2013 | Stone .................. A61C 17/065 210/136 |
| 2014/0154641 A1 | 6/2014 | Bogen |
| 2015/0320638 A1 | 11/2015 | Becker |
| 2018/0098831 A1 | 4/2018 | Mozzicato |
| 2022/0211476 A1 | 7/2022 | Stolarik |

FOREIGN PATENT DOCUMENTS

| | | |
|---|---|---|
| WO | WO 1983/002720 A1 | 8/1983 |
| WO | WO 1994/016643 A1 | 8/1994 |
| WO | WO 2018/006106 A1 | 1/2018 |

OTHER PUBLICATIONS

Solmetex; "Solmetex Hg5 Amalgam Separator, Type 2—Maximum Flow = 1000 ml/min: Installation and Maintenance Instructions"; Northborough, Massachusetts; Revised Apr. 27, 2012 (8 pages).

ASME USAS B17-1; "Keys and Keys Seals": American Society of Mechanical Engineers; USA Standard, 1967 (Reaffirmed 2013).

Defendant DRNA's Motion to Dismiss in Solmetex, LLC v. Dental Recycling North America, Inc., Civil Action No. 1:23-cv-00602-MN, D.I. 10; Aug. 7, 2023 (2 pages).

Defendant DRNA's Opening Brief in Support of its Motion to Dismiss in Solmetex, LLC v. Dental Recycling North America, Inc., Civil Action No. 1:23-cv-00602-MN, D.I. 12-1 (26 pages).

U.S. Pat. No. 11,660,175; Ex. 1 to Defendant DRNA's Opening Brief in Support of its Motion to Dismiss in Solmetex, LLC v. Dental Recycling North America, Inc., Civil Action No. 1:23-cv-00602-MN, D.I. 12-1 (27 pages).

Excerpts of the File History for U.S. Pat. No. 11,660,175; Ex. 2 to Defendant DRNA's Opening Brief in Support of its Motion to Dismiss in Solmetex, LLC v. Dental Recycling North America, Inc., Civil Action No. 1:23-cv-00602-MN, D.I. 12-2 (347 pages).

"Cartridge 2—Compatible with Solmetex® NXT Hg5® Only"; Ex. 3 to Defendant DRNA's Opening Brief in Support of its Motion to Dismiss in Solmetex, LLC v. Dental Recycling North America, Inc., Civil Action No. 1:23-cv-00602-MN, D.I. 12-3; retrieved from https://drna.com/products/Cartridge-2-Compatible-with-Solmetex-r-NXT-Hg5-r--ONLY-p454946180 on Oct. 10, 2023 (6 pages).

Https://vimoe.com/509905162, "Replacing Your Amalgam Separator Cartridge with DRNA's Generic Cartridge", included on https://drna.com/products/Cartridge-2-Compatible-with-Solmetex-r-NXT-

(56) References Cited

OTHER PUBLICATIONS

Hg5-r-**-ONLY-p454946180; Ex. 4 to Defendant DRNA's Opening Brief in Support of its Motion to Dismiss in Solmetex, LLC v. Dental Recycling North America, Inc., Civil Action No. 1:23-cv-00602-MN, D.I. 12-4; retrieved on Oct. 10, 2023 (2 pages).
Petition for Post Grant Review of U.S. Pat. No. 11,660,175 in Case No. PGR2023-00055 (196 pages).
Ex. 1001 to Petition in Case No. PGR2023-00055, U.S. Pat. No. 11,660,175 B2 to Mozzicato (26 pages).
Ex. 1002 to Petition in Case No. PGR2023-00055, File History of U.S. Pat. No. 11,660,175 to Mozzicato (346 pages).
Ex. 1003 to Petition in Case No. PGR2023-00055, Declaration of Dr. Jason Janet in Support of the Petition for Post Grant Review of U.S. Pat. No. 11,660,175, dated Sep. 29, 2023 (12 pages).
Ex. 1004 to Petition in Case No. PGR2023-00055, Declaration of Darwin Moreira in Support of the Petition for Post Grant Review of U.S. Pat. No. 11,660,175, dated Sep. 29, 2023 (12 pages).
Ex. 1005 to Petition in Case No. PGR2023-00055, Photos of DRNA Generic Cartridge 2 and corresponding components (2 pages).
Ex. 1006 to Petition in Case No. PGR2023-00055, "Cartridge 2 Installation Instructions" (2 pages).
Ex. 1007 to Petition in Case No. PGR2023-00055, Photos of Solmetex NXT Hg5 Collection Container and corresponding components (26 pages).
Ex. 1008 to Petition in Case No. PGR2023-00055, Solmetex NXT Hg5 Collection Container Replacement & Recycling Procedure (8 pages).
Ex. 1009 to Petition in Case No. PGR2023-00055, Solmetex NXT Hg5 Collection Container Shipping and Recycling Information (1 page).
Ex. 1010 to Petition in Case No. PGR2023-00055, CN 102989232 A to Liu et al. ("Liu") and Certified English Translation Thereof (17 pages).
Ex. 1011 to Petition in Case No. PGR2023-00055, CA 2356902 A1 to Boyd ("Boyd") (26 pages).
Ex. 1013 to Petition in Case No. PGR2023-00055, "Solmetex NXT-Hg5 Amalgam Separator Installation and Operations Manual," Exhibit B to Complaint filed in Solmetex, LLC v. Dental Recycling North America, Inc., Civil Action No. 1:23-cv-00602-UNA, D.I. 1, Ex. B; Jun. 1, 2023 (9 pages).
Ex. 1014 to Petition in Case No. PGR2023-00055, U.S. Patent Publication No. 2021/0106412 A1, published Apr. 15, 2021, which is the published application of U.S. Appl. No. 16/941,522 (32 pages).
Ex. 1015 to Petition in Case No. PGR2023-00055, Vermont Dental Amalgam Separator Pilot Project; Vermont Department of Environmental Conservation; Aug. 2004 (22 pages).
Ex. 1016 to Petition in Case No. PGR2023-00055, Medentex, "Amalsed Silver Powered by Apavia—Installation & Operating Manual"; publication date not available (20 pages).
Ex. 1017 to Petition in Case No. PGR2023-00055, Tech West Eco-Star Retail Price Index, revised May 18 (20 pages).
Ex. 1018 to Petition in Case No. PGR2023-00055, "Solmetex History Into Amalgam & Mercury Removal & Recycling Productions"; retrieved from https://solmetex.com/history/; Sep. 19, 2023 (5 pages).
Ex. 1019 to Petition in Case No. PGR2023-00055, "Solmetex NXT Hg5 Series Amalgam Separator FAQs"; retrieved from https://solmetex.com/faqs-nxt/; Sep. 19, 2023 (8 pages).
Ex. 1020 to Petition in Case No. PGR2023-00055, Defendant DRNA's Opening Brief in Support of its Motion to Dismiss in Solmetex, LLC v. Dental Recycling North America, Inc., Civil Action No. 1:23-cv-00602-MN, D.I. 11; Aug. 7, 2023 (26 pages).
Ex. 1021 to Petition in Case No. PGR2023-00055, Plaintiff Solmetex, LLC's Opposition to Defendant Dental Recycling North America, Inc.'s Rule 12(b)(6) Motion to Dismiss for Failure to State a Claim in in Solmetex, LLC v. Dental Recycling North America, Inc., Civil Action No. 1:23-cv-00602-MN, Civil Action No. 1:23-00602-MN, D.I. 14; Aug. 21, 2023 (27 pages).
Ex. 1022 to Petition in Case No. PGR2023-00055, Defendant DRNA's Reply in Support of its Motion to Dismiss in in Solmetex, LLC v. Dental Recycling North America, Inc., Civil Action No. 1:23-cv-00602-MN, Civil Action No. 1:23-00602-MN, D.I. 15; Aug. 28, 2023 (16 pages).
Ex. 1023 to Petition in Case No. PGR2023-00055, "DRNA Website on Cartridge 2"; retrieved from https://drna.com/products/Generic-Amalgam-Separator-Cartridges-c130499018; Sep. 19, 2023 (5 pages).
Ex. 1024 to Petition in Case No. PGR2023-00055, "DRNA Contact US Webpage"; retrieved from https://drna.com/contact/; Sep. 19, 2023 (3 pages).
Ex. 1025 to Petition in Case No. PGR2023-00055, "Solmetex NXT Hg5 Series of Amalgam Separators"; retrieved from https://solmetex.com/hg5-series-products/#hg5; Sep. 19, 2023 (11 pages).
Ex. 1026 to Petition in Case No. PGR2023-00055, "NXT Separator Installation and Operations Manual"; retrieved from https://solmetex.com/wp-content/uploads/2021/11/NXT-Hg5-Install-Ops-Manual-11.2021_FINAL.pdf; publication date not available (8 pages).
Ex. 1027 to Petition in Case No. PGR2023-00055, "Solmetex NXT Collection Container Change-Out video"; retrieved from https://www.youtube.com/watch?v=WFAFuBGZH1w; Sep. 19, 2023 (2 pages).
Ex. 1028 to Petition in Case No. PGR2023-00055, "Solmetex Contact US Webpage"; retrieved from https://solmetex.com/contact-us/; Sep. 19, 2023 (6 pages).
Ex. 1029 to Petition in Case No. PGR2023-00055, U.S. Pat. No. 10,918,982 to Sutton (22 pages).
Ex. 1030 to Petition in Case No. PGR2023-00055, U.S. Pat. No. 8,007,669 to Chernoff (8 pages).
Ex. 1031 to Petition in Case No. PGR2023-00055, U.S. Pat. No. 3,615,016 to Soriente (8 pages).
Ex. 1032 to Petition in Case No. PGR2023-00055, German Patent No. DE 3737002 C1 to Becker (18 pages).
Ex. 1033 to Petition in Case No. PGR2023-00055, Chinese Patent Publication No. 107417069 A (15 pages).
Ex. 1034 to Petition in Case No. PGR2023-00055, Memorandum Order in Personal Genomics Taiwan, Inc. v. Pacific Biosciences of California, Inc., Civil Action No. 19-1810-GBW-MPT (D. Del. Sep. 15, 2022) (4 pages).
Ex. 1035 to Petition in Case No. PGR2023-00055, Memorandum Order in WSOU Investments, LLC d/b/a Brazos Licensing and Development v. NetGear, Inc., Civil Action Nos. 21-1117-MN-CJB and 21-1120-MN-CJB 9 (D. Del. Nov. 30, 2022) (4 pages).
Ex. 1036 to Petition in Case No. PGR2023-00055, Memorandum Order in Consumeron, LLC v. MapleBear Inc. d/b/a Instacart, Civil Action No. 21-1147-GBW-MPT (D. Del. May 12, 2023) (5 pages).
Ex. 1037 to Petition in Case No. PGR2023-00055, Federal Court Management Statistics—Comparison Within Circuit, retrieved from https://www.uscourts.gov/statistics/able/na/federal-court-management-statistics/2022/03/31-3; Mar. 31, 2022 (4 pages).
Order from District of Delaware Denying DRNA's Motion to Dismiss in Case No. 23-602 (MN) (D. Del. Oct. 18, 2023) (2 pages).
Plaintiff Solmetex, LLC's Opposition to Defendant Dental Recycling North America, Inc.'s Rule 12(B)(6) Motion to Dismiss For Failure to State a Claim in Case No. 23-602 (Mn) D.14 (27 pages).
Complaint filed in Solmetex, LLC v. Dental Recycling North America, Inc., Civil Action No. 1:23-cv-00602-UNA, D.I. 1; dated Jun. 1, 2023 (58 pages).
Defendant's Answer, Defenses, and Counterclaims to Solmetex, LLC's Complaint, filed in Solmetex, LLC v. Dental Recycling North America, Inc., Civil Action No. 1:23-cv-00602-UNA, D.I. 18; dated Nov. 1, 2023 (40 pages).

* cited by examiner

DETACHABLE RECYCLING CONTAINER

RELATED APPLICATIONS

This patent application claims priority from provisional patent application Ser. No. 62/414,712, filed on Oct. 29, 2016; and provisional patent application Ser. No. 62/406,990, filed on Oct. 12, 2016. This application further claims priority from patent application Ser. No. 29/667,212, filed Oct. 19, 2018, which is a continuation of Ser. No. 29/585,659, filed on Nov. 28, 2016, now patent number D835,778. This patent application further claims priority from patent application Ser. No. 29/585,674, filed on Nov. 28, 2016. This patent application further claims priority from patent application Ser. No. 29/672,887, filed on Dec. 10, 2018, which is a continuation of patent application Ser. No. 29/585,668, filed on Nov. 28, 2016, now patent number D835,779. This patent application further claims priority from patent application Ser. No. 29/577,701, filed on Sep. 14, 2016. This patent application further claims priority from patent application Ser. No. 29/567,544, filed on Jun. 9, 2016. This patent application further claims priority from patent application Ser. No. 29/671,943, filed on Nov. 30, 2018, which is a continuation of patent application Ser. No. 29/565,622, filed on May 23, 2016, now issued patent D835,264.

FIELD OF THE INVENTION

This invention relates to systems and apparatus suitable to remove particles from effluent waste, and particularly, to remove amalgam and other metallic particles and other abrasive solids from dental office suction effluent. The system also comprises a self contained recycling container to facilitate customer regulatory compliance and environmental safeguards.

BACKGROUND OF THE INVENTION

Dental amalgam is a dental filling material used to fill cavities caused by tooth decay. It has been used for more than 150 years in hundreds of millions of patients around the world.

Dental amalgam is a mixture of metals, consisting of liquid (elemental) mercury and a powdered alloy composed of silver, tin, and copper. Approximately 50% of dental amalgam is elemental mercury by weight. The chemical properties of elemental mercury allow it to react with and bind together the silver/copper/tin alloy particles to form an amalgam. See http://www.fda.gov/MedicalDevices/ProductsandMedical_Procedures/DentalProducts/DentalAmalgam/ucm171094.htm, accessed Sep. 9, 2016.

Amalgam is used less often than in the past, mostly because tooth-colored materials now can be used. However, the newer materials can't be used for all dental situations, amalgam is less costly than newer materials and it lasts longer, especially in teeth that undergo a lot of pressure and wear from chewing.

Better dental health overall coupled with increased demand for more modern alternatives such as resin composite fillings (which match the tooth color), as well as public concern about the mercury content of dental amalgam, have resulted in a steady decline in dental amalgam use in developed countries, though overall amalgam use continues to rise worldwide. Stein, PS; Sullivan, J; Haubenreich, JE; Osborne, PB (2005). "Composite resin in medicine and dentistry". Journal of long-term effects of medical implants. 15 (6): 641-54. doi:10.1615/jlongterrneffrnedirnplants.v15.i6.70. PMID 16393132.

Although amalgams are less frequently used in developed countries for new dental fillings than in the past, amalgams continue to make up a portion of the particle component of dental office effluent mainly because of the fact that old fillings made of amalgams are drilled out and removed in the effluent waste when new fillings are effected to replace the old. Further, as noted above, even under current dental practice, an amalgam is preferred for some tooth filling situations.

Because mercury is a poison that can accumulate in living tissues and can pose a health hazard to species in a food chain exposed to mercury-containing compounds, and since humans are inevitably at the end of the food chain, it follows that effluent containing amalgams can pose a health hazard to the community at large. Also, certain metals such as silver are commercially valuable if recovered in quantity. For those reasons, it is desirable to devise systems, apparatus and processes for removing amalgams from dental office effluent and efficiently recycling those amalgams.

In addition to removing amalgams, other matter disposed into dental office suction effluent includes aluminum oxides used in air abrasion treatments and other solid waste material. These solid materials tend to wear out or damage vacuum pumps and other equipment downstream of the dental chair suction apparatus, and also constitute effluent water contaminants. Therefore, it is desirable for the apparatus to remove solid abrasive material and other particulate waste from the dental office suction effluent.

The World Health Organization also points out that amalgam separators, installed in the waste water lines of many dental offices, dramatically decrease the release of mercury into the public sewer system. However, critics say that the separators are still not mandatory in some states of the United States. "Purchasing, installing and operating dental amalgam separators: Practical issues". The Journal of the American Dental Association. 134 (8): 1054-65. doi: 10.14219/jada.archive.2003.0319. PMID 12956345. Recently, the EPA has enacted nation-wide regulations requiring amalgam separators in dental offices.

Previously known apparatus for removing amalgam particles from dental office suction effluent are known to include a collecting tank for collecting a day's accumulation of suction effluent from one or more sources of such waste. The waste is sucked from the dental chair suction apparatus and into the collecting tank by a vacuum pump. When the vacuum pump is turned off, an outlet valve is opened and the accumulated waste is deposited into a separation device intended to separate metal particles from the effluent liquid. Flow into the separation device is induced by the head of fluid in the collecting tank. Particles passing through the separation device are separated from the waste by gravity and settle to the bottom of the separation device. The flow rate is dependent on the head inside the collecting tank; as the head diminishes, the flow rate also diminishes. The changes in flow rate are undesirable because the particle separation rate is affected, and the system becomes prone to plugging when the flow rate decreases. Also, since the waste can be deposited only when the vacuum pump is off, waste is usually moved to the separation device at the end of the day. As a result, the collecting tank and separation device tend to be undesirably large and the whole process is time consuming.

Another known apparatus is a centrifuge type system that separates heavier metal particles from effluent liquid by collecting the particles at the peripheral wall of the centrifuge. This apparatus does not effectively separate lighter particles, and is expensive to purchase and operate due to the complexity of its mechanical parts.

Yet another known apparatus uses a dedicated mechanical pump to suction waste liquids through a separator device. Again, a dedicated pump can be expensive to purchase and to maintain, and can be undesirably space-consuming.

Such known systems can become quite complex, unwieldy and expensive, as for example that disclosed in U.S. Pat. No. 5,885,076 granted 23 Mar. 1999. It teaches the use of sedimentation, co-precipitation and filtration in an expensive complicated apparatus that is probably economical, if at all, only for relatively large installations such as a military base dental complex.

U.S. Pat. Nos. 6,692,636; 6,596,754 are patents that disclose systems for removing amalgam from dental office suction effluent.

After collecting the amalgam and other solid waste the dentist is left with the problem of what to do with the waste. Either the dentist has to deal with his own hazardous waste or he can send his collected material to a recycler. In either case, the "collection container" needs to be disposable and easily replaceable.

Existing recycling programs generally require the provision of bulky shipping materials and the delivery of those materials to the dentist for every full container. If such materials are not provided and the materials are not properly recycled a large part of the benefit of collecting the amalgam waste can be lost. It is important that the waste is recycled under federal guidelines in order to make sure the full benefits of amalgam separation are achieved.

Additionally, containers for collection, such as dental amalgam recycling systems, can be compromised by incorrect installation or misalignment, which can cause O-rings to deform and/or seal irregularly, and result in leakage.

SUMMARY OF THE INVENTION

The present invention overcomes many of the shortcomings of the prior technology and achieves further advantages that will be apparent after reviewing the following detailed description.

In one aspect, the invention comprises a dental amalgam recycling system for recycling particles from a dental liquid effluent drawn from a suctioning device. In certain embodiments, the dental amalgam recycling system of the invention comprises:

(a) an air-water separator tank for receiving said effluent, said air-water separator tank having an air-water separator tank inlet in fluid communication with said suctioning device, an air-water separator tank liquid effluent outlet and an air-water separator tank air outlet;

(b) a detachable recycling container, said recycling container acting primarily under the influence of gravity to cause settlement of said particles; said recycling container having a recycling container effluent inlet port connected to said air-water separator tank liquid effluent outlet and said recycling container further having an effluent outlet port;

(c) wherein the air-water separator tank also includes an internal suction conduit;

(d) wherein the recycling container comprises threads;

(e) wherein the recycling container effluent inlet port and the recycling container outlet port are not the same height.

In certain embodiments, the dental amalgam recycling system further comprises (f) a threaded shipping cap, wherein the threads of the shipping cap and the threads of the recycling container are complementary such that, when the shipping cap is fitted in place, the shipping cap forms a tight seal with said recycling container.

While in use, the dental amalgam recycling system is functionally associated with a vacuum pump having a vacuum pump inlet. The vacuum pump is typically a pre-existing part of the dental office facility. In particular embodiments, the dental amalgam recycling system is physically connected with a vacuum pump via a suction conduit in the air-water separator. In certain preferred embodiments, the suction conduit is an internal suction conduit within the air-water separator.

In certain embodiments, the dental amalgam recycling system of the invention further comprise a first plug for said recycling container inlet port and a second plug for said recycling container effluent outlet port. Said first and second plugs may be held tightly in place by said threaded shipping cap when said shipping cap is fitted in place.

In certain embodiments, the dental amalgam recycling system of the invention further comprise an O-ring that provides an air and effluent tight seal when said shipping cap is fitted in place.

In certain embodiments, the invention comprises a container, useful as a dental amalgam recycling container, comprising threads for attachment of a shipping cap. In certain embodiments, the dental amalgam recycling container further comprises two plugs held in place by said shipping cap and an O-ring fitted in an O-ring groove to prevent leaks. The dental amalgam recycling containers of the present invention may further comprise a two tier cap that enables people with hands of different sizes to grip the cap and tighten to achieve a very tight seal.

In certain embodiments, the invention comprises an adapter for an air-water separator tank, wherein the adapter enables a recycling container without compatible effluent ports to attach to an air-water separator tank. Said air-water separator tank may comprise, for example, a component of a dental amalgam recycling system, as described above. In certain embodiments, the adapter may comprise threads. In alternative embodiments, the adaptor may be without threads.

As described above, the potential for leakage exists in a collection canister such as a recycling container used in the dental amalgam recycling systems described herein. Such leakage may occur, for example, due to incorrect installation, or due to misalignment of a container and its intended mating partner, such as the air-water separation tank or its intended cap, such as a threaded shipping cap, which may cause O-rings to deform and/or seal irregularly. In order to address this problem and/or reduce the potential for leakage, a collection canister, such as a recycling container used in a dental amalgam recycling system, may have one or more irregular 'keyways' cast into its outside top mating surface, and the intended mating partner, such as the air-water separation tank, or the shipping cap, may have one or more corresponding 'key(s)' be cast into its mating surface, such that the key(s) and keyway(s) must be aligned in order for the collection canister (e.g., the recycling container) and its mating partner (e.g., the air-water separation tank; or the shipping cap) to mate properly. This key/keyway system can help ensure even pressure across the entire circumference of the O-ring surface on each port. Similarly, such key(s) and keyway(s) may be used to ensure proper replacement of the container and/or the air-water separation tank, such that incorrect replacement can be avoided or minimized.

BRIEF DESCRIPTION OF THE DRAWINGS

1-Backplate
2-Waste Inlet (from dental practice)
3-Air/water Separator Top
4-Top Support Bracket
5-Air/Water Separation Tank
6-Suction tube
7-Air/Water Separator Base
8-Outlet Tube (to vacuum system)
9-Recycling Container Top Portion
10-Lower Support Bracket
11-Restrictor
12-Detachable Recycling Container
13-Retaining Pins (2)
14-air-water separator tank effluent outlet port
15-recycling container inlet port
16-recycling container outlet port
17-recycling container threads
18-two tier recycling cap
19-O-ring groove
20-cap plugs
21-O-ring

DETAILED DESCRIPTION WITH REFERENCE TO THE DRAWINGS

According to one aspect of the instant invention, an apparatus is provided for removing and recycling metal-containing particles and other waste particles from effluent, particularly effluent from a dental office. While herein the term "metal particles" may frequently be employed, it is contemplated that the apparatus is capable of separating other solid particles from effluent liquid.

According to one aspect of the invention, an apparatus for removing metal particles and other solid particles from liquid suction effluent can be installed in a dental office using a pre-existing suction/vacuum pump system. The apparatus may share a common vacuum pump with conventional dental chair suction apparatus, without interrupting the use of suction equipment at the dental chairs.

Removal of solid particles from liquid suction effluent is effected by sedimentation.

In accordance with a one embodiment of the invention, the dental office suction effluent is passed from dental chair suction equipment outlets to an air water separator tank via a suitable inlet port for the tank. The air-water separator tank in turn passes effluent into a sedimentary deposit tank, closed on all sides when in use and preferably readily detachable for emptying or replacement.

In certain aspects of the instant invention the sedimentary deposit tank has a secondary function as a recycling container. In another aspect of the invention this recycling container can have features built in to make recycling easier and to reduce the amount of packaging and waste in the recycling system.

In another embodiment of the invention designed to minimize the space required to install the amalgam recycling system the air-water suction tube is internalized—within the air-water separator tank.

Figure 1:
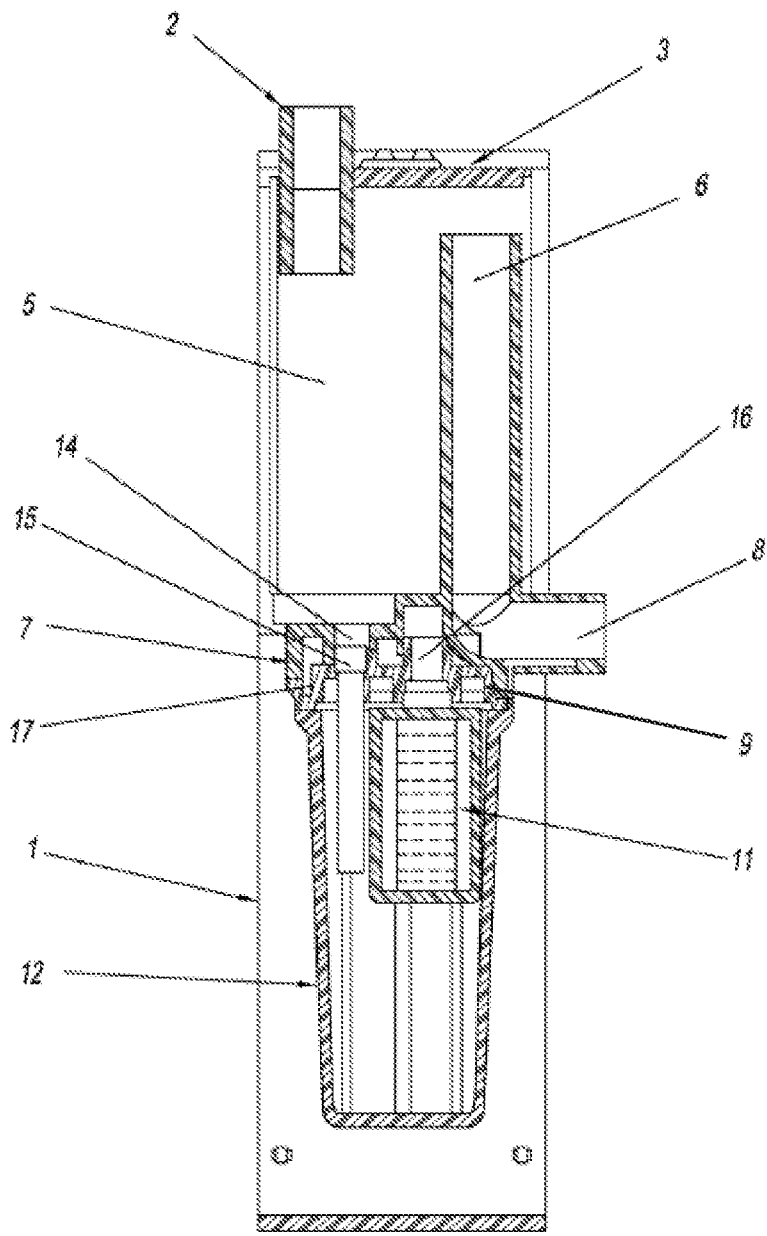
FIG. 1 is a schematic front view of an embodiment of particle removal and recycling apparatus according to the invention, for particular use in a dental office.
Figure 2:
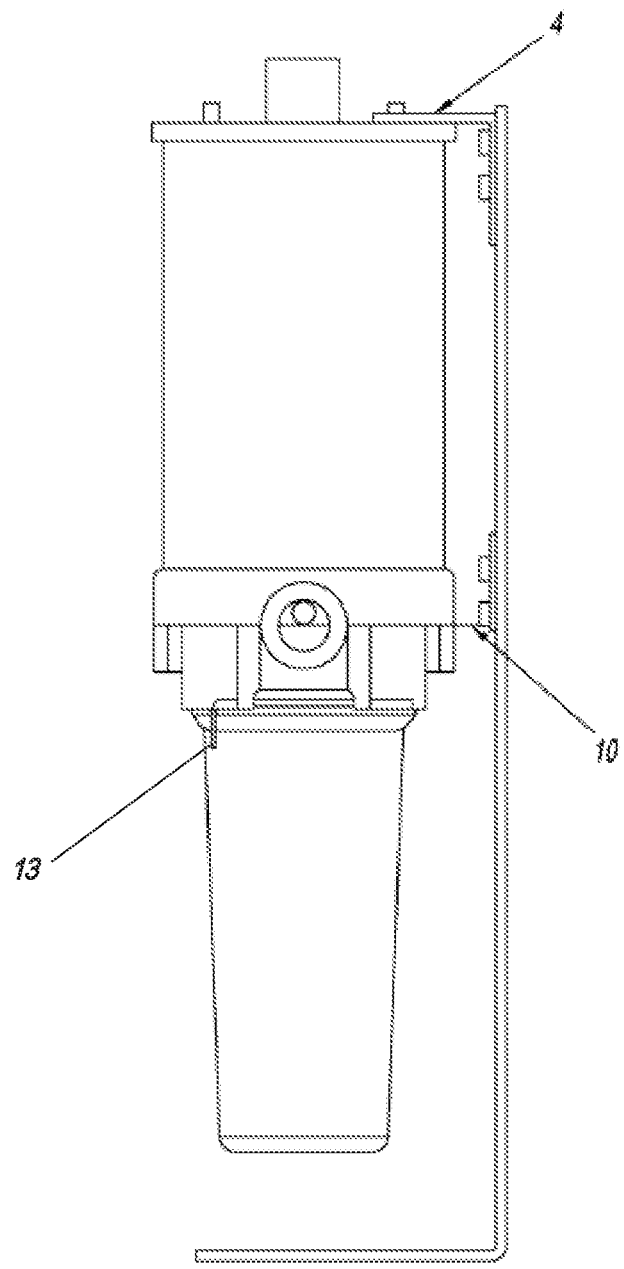
FIG. 2 is a schematic side view of an embodiment of particle removal and recycling apparatus according to the invention, for particular use in a dental office.

FIG. 1 and FIG. 2 shows two views of the separation apparatus according to the present invention in detail. Effluent from the dental chairs and a quantity of air are sucked through a suction apparatus exhaust conduit, through an air-water separator tank inlet 2, and thence into an air-water separator tank 5. The liquid effluent passes out of the air-water separator tank 5 via air-water separator tank outlet port 14, while air passes downstream via the air suction tube 6 while maintaining constant vacuum upstream of amalgam separator.

The air-water separator tank effluent outlet port 14 passes effluent by gravity out of the air-water separator tank 5 and into the detachable recycling container 12 through the recycling container inlet port 15 on the container top portion 9 for target particle separation by sedimentation. After the effluent passes through the inlet port 15 and through the container inlet conduit in the interior volume of the main body of the detachable recycling container 12, solids settle and accumulate in the bottom of the interior volume of the main body of the detachable recycling container 12. Liquid content of waste flows primarily by gravity, although intermittently assisted by vacuum through Restrictor 11 which slows the flow rate of liquid to assist in sedimentation process and ultimately "clean" effluent discharge through the recycling container outlet port 16 on the container top portion 9.

Outlet ports 16 and inlet port 15 can be a variety of shapes and sizes, square, oval (as depicted), round or even more unusual shapes like a star. Preferred ports are those that provide a tight seal, allow for easy removal, and do not break. Oval or round are preferred embodiments. Round are most preferred.

A vacuum at the outlet tube 8 is generated when the vacuum pump is operating, thereby sucking air out of the air-water separator tank 5 via suction tube 6 while maintaining vacuum upstream of amalgam separator apparatus. Effluent from the recycling container 12 passes through the restrictor 11 where remaining non-settable fine particles are removed from the effluent and into the recycling container outlet port 16 to be discharged from the apparatus via common outlet tube 8. Matter sucked by the vacuum pump, generally free of removed solids, is discharged via vacuum pump into a municipal drain of the public sewage system.

The system is provided with a simple back plate 1 for easy dental office placement as well as removable retaining pins 13 that engage radially protruding structures of the recycling container to ensure the recycling container does not detach from the air-water separation tank 5 when there is no vacuum in the system.

In certain embodiments, the recycling container ports 16 and 15 may be different heights in order to aid in alignment of the detachable recycling container 12 in the air-water separator base 7. In a preferred embodiment, the outlet port 16 engages before the inlet port 15 while during removal the inlet port 15 disengages first. This causes a small volume of fluid to be pulled out of the collection container back into air-water separator tank 5 creating head space and eliminating upward force of vacuum which eases removal of recycle container 12 by operator. Existing devices require rocking, wiggling or applying extensive down force for removal of recycle container 12.

In one preferred embodiment of the invention designed to minimize recycling costs and waste, the recycling container/sedimentary deposit tank has threads 17 built into the generally cylindrical upper region of the container top portion 9 to enable the addition of a liquid tight top for shipping.

Figure 3A:
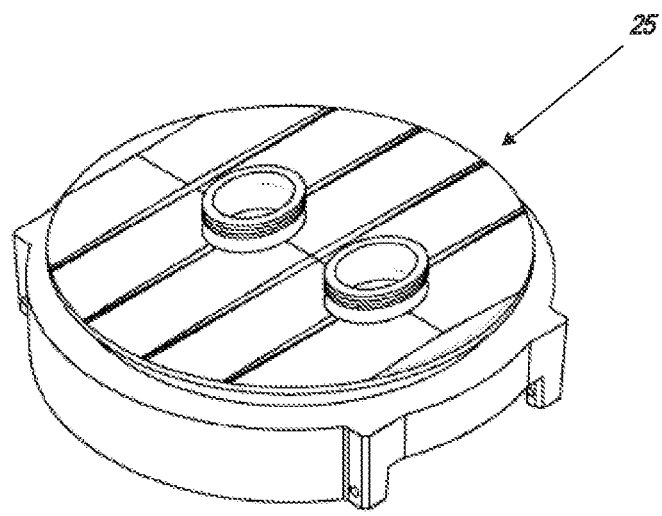
FIG. 3a is a schematic view of an embodiment of a universal adapter for fitting various different sized recycling containers to the air-water separator of the present invention.
Figure 3B:
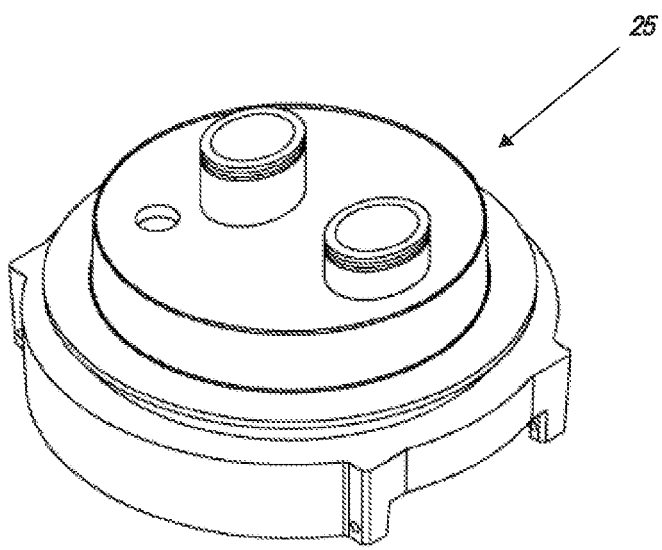
FIG. 3b is a schematic view of an alternative embodiment of a universal adapter for fitting various different sized recycling containers to the air-water separator of the present invention.

FIG. 3 shows a schematic diagram of an adapter 25 according to the invention to enable the use of recycling containers from a variety of sources that are lacking in correctly shaped ports 16 and 15 or otherwise are unable to fit the air-water separator tank 5 according to the invention due to shape differences.

Figure 4A:
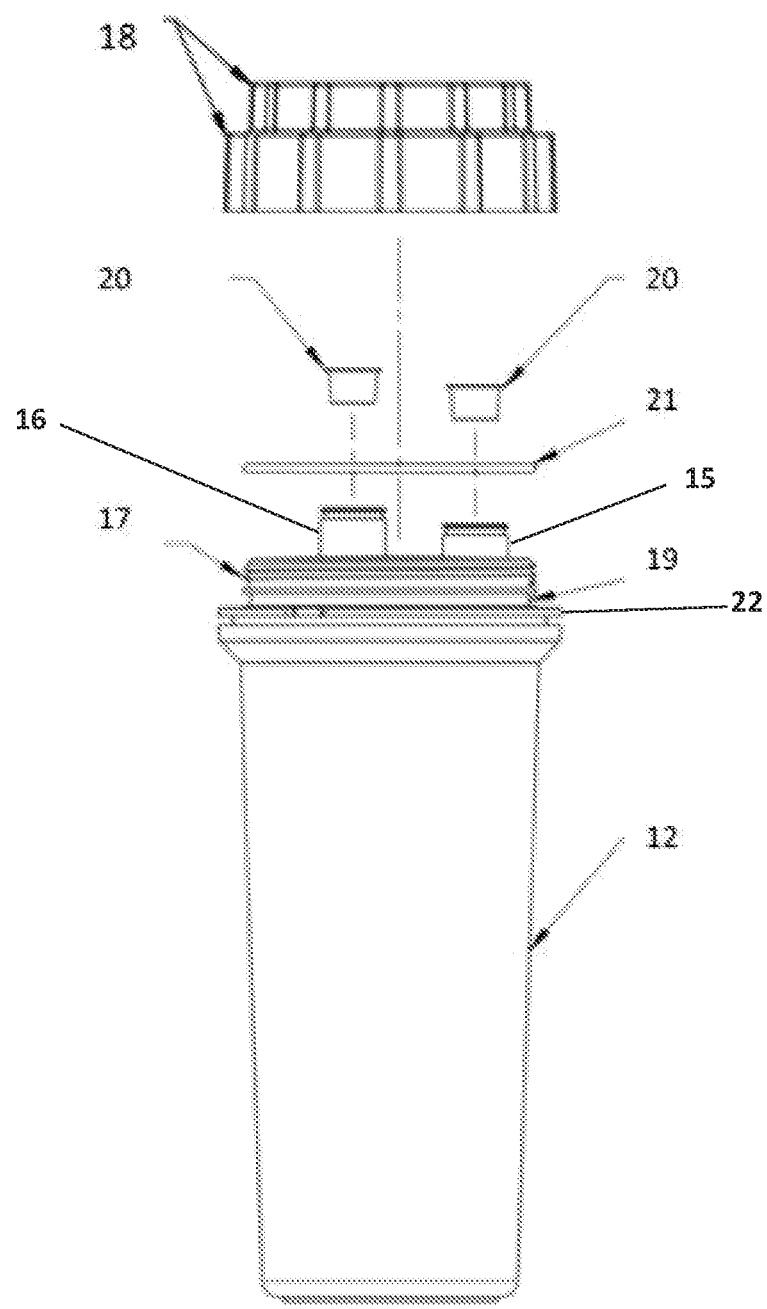
FIG. 4a is a schematic view of an embodiment of a recycling container and cap system of the invention.
Figure 4B:
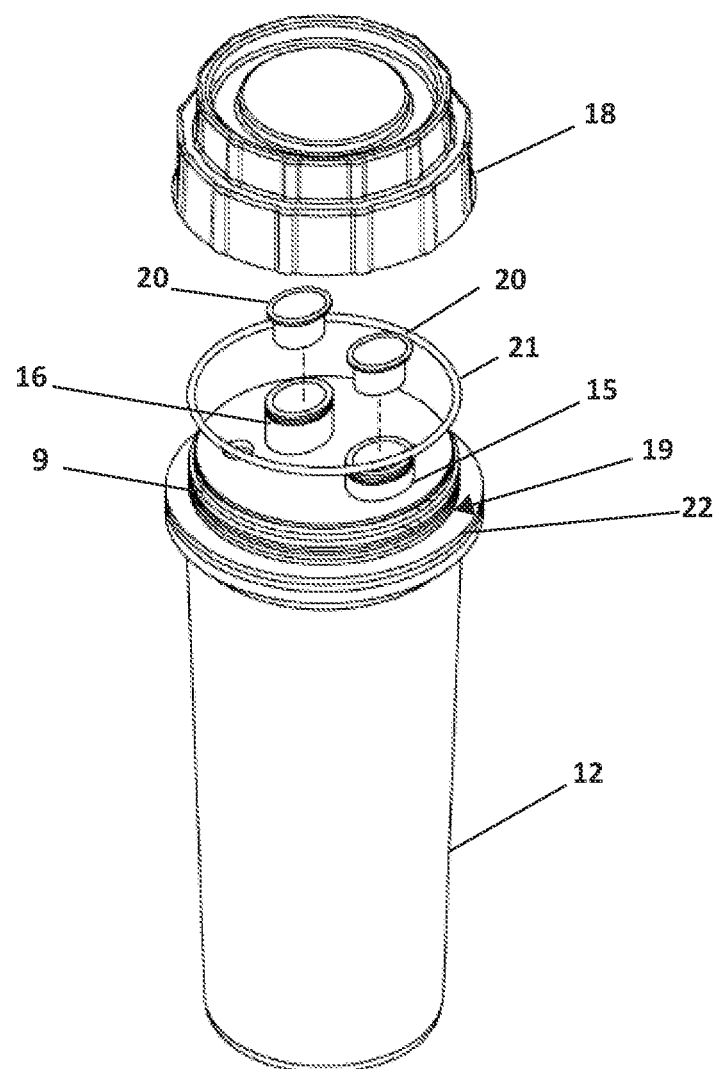
FIG. 4b is a schematic perspective depiction of an embodiment of a recycling container and cap system of the invention.
Figure 5A:
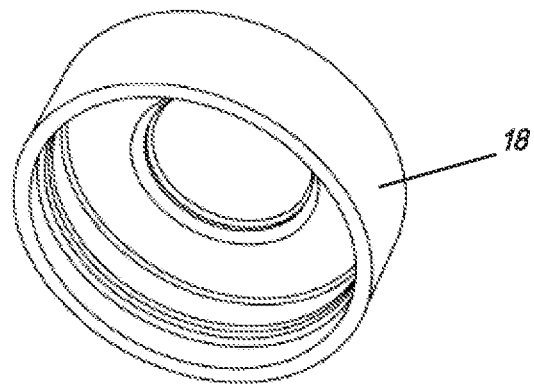
FIG. 5a is a schematic inside view of an embodiment of a recycling cap for the recycling containers of the invention.
Figure 5B:
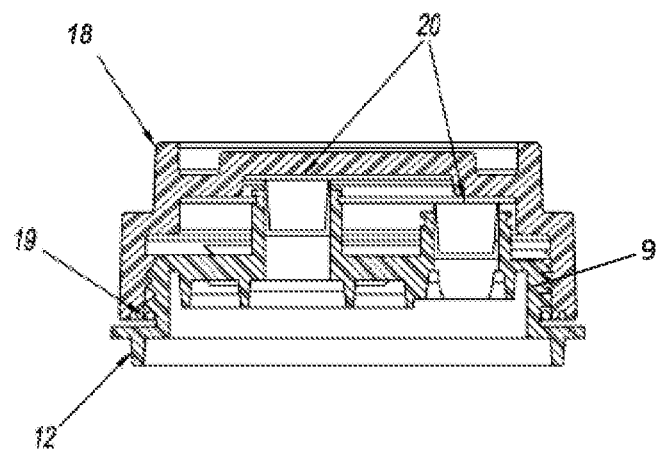
FIG. 5b is a schematic depiction of a recycling cap according to the invention fitting on a partial view of a recycling container according to the invention.
Figure 6A:
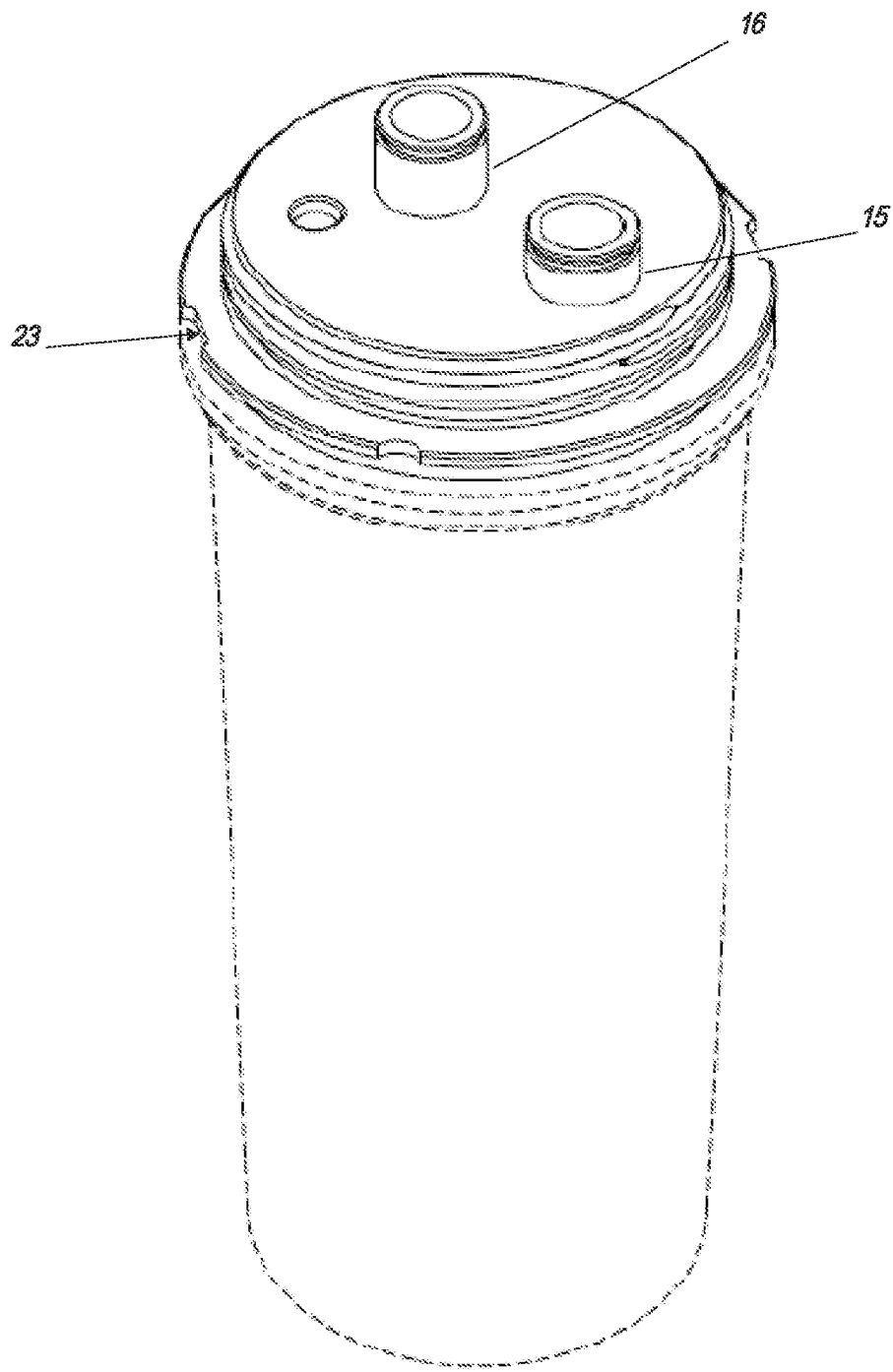
FIG. 6A is a schematic view of a first embodiment of a detachable container according to the present invention, viewing the top of the container at an angle.
Figure 6B:
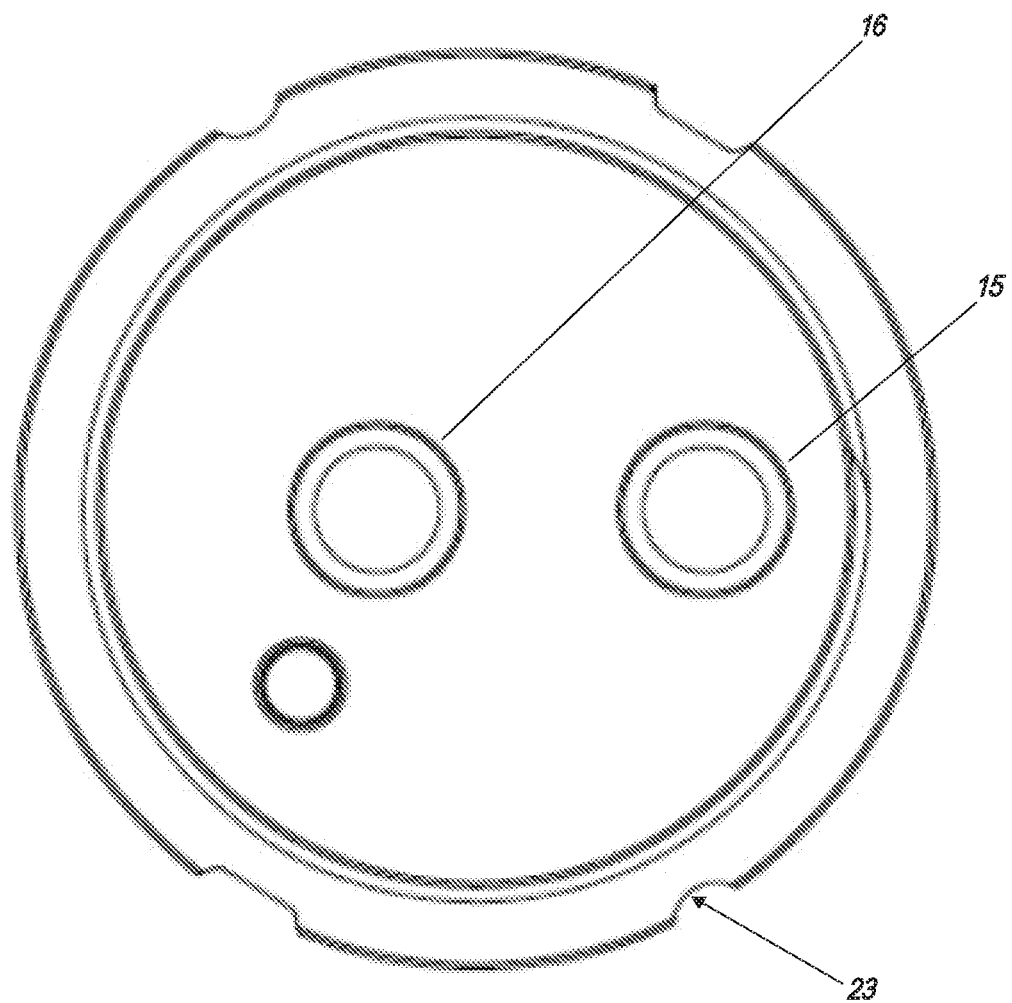
FIG. 6B is a schematic view of the same embodiment, viewing the top of the container from directly above.
Figure 7A:
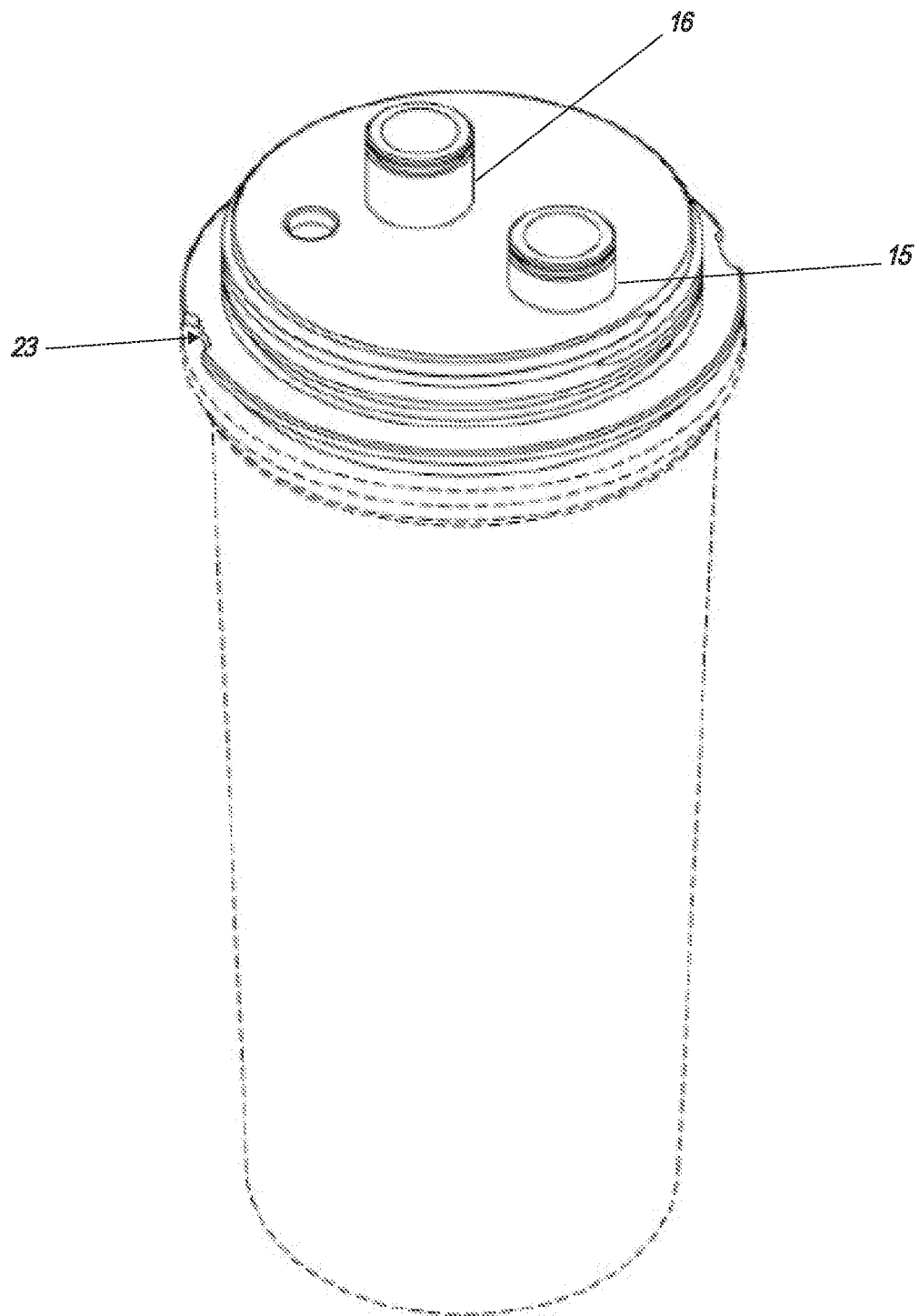
FIG. 7A is a schematic view of a second embodiment of a detachable container according to the present invention, viewing the top of the container at an angle.
Figure 7B:
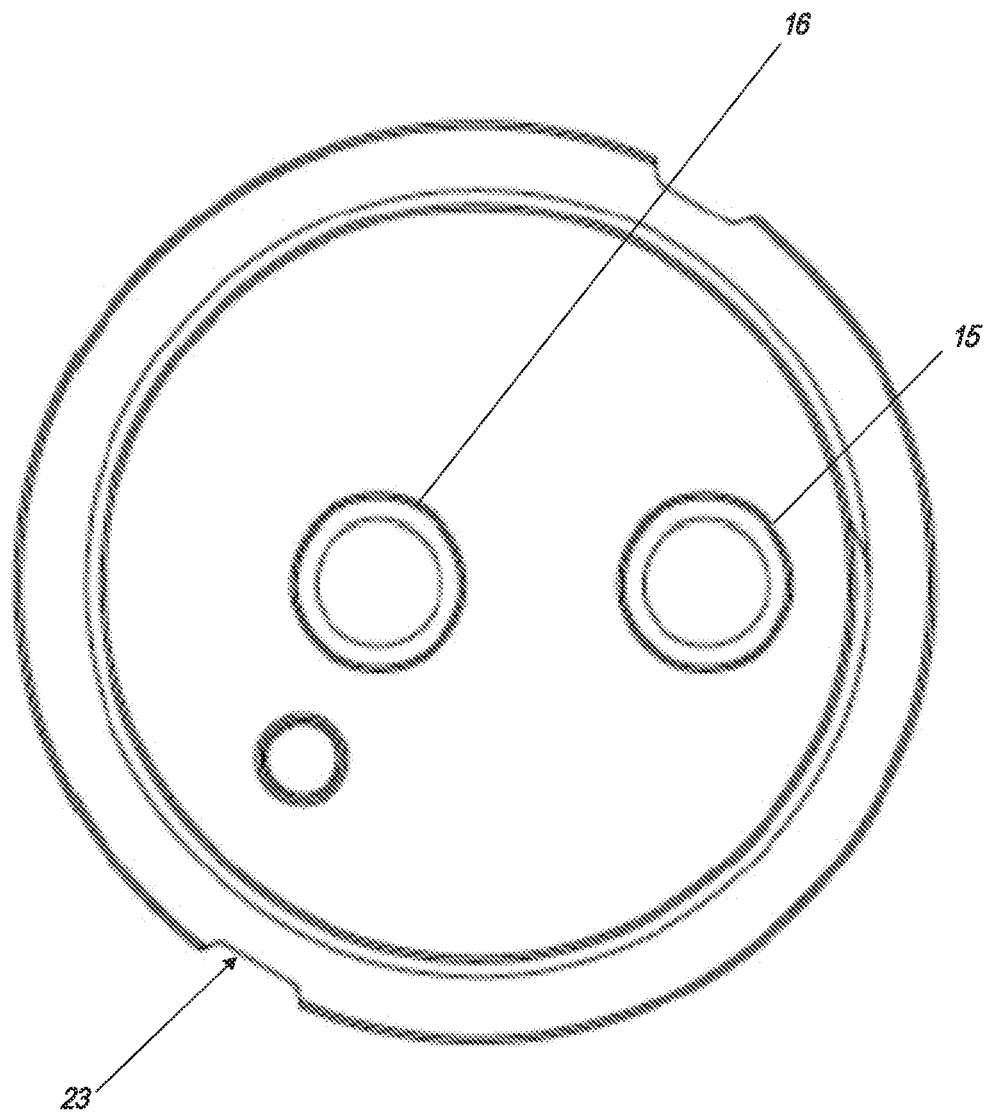
FIG. 7B is a schematic view of the same embodiment, viewing the top of the container from directly above.
Figure 8A:
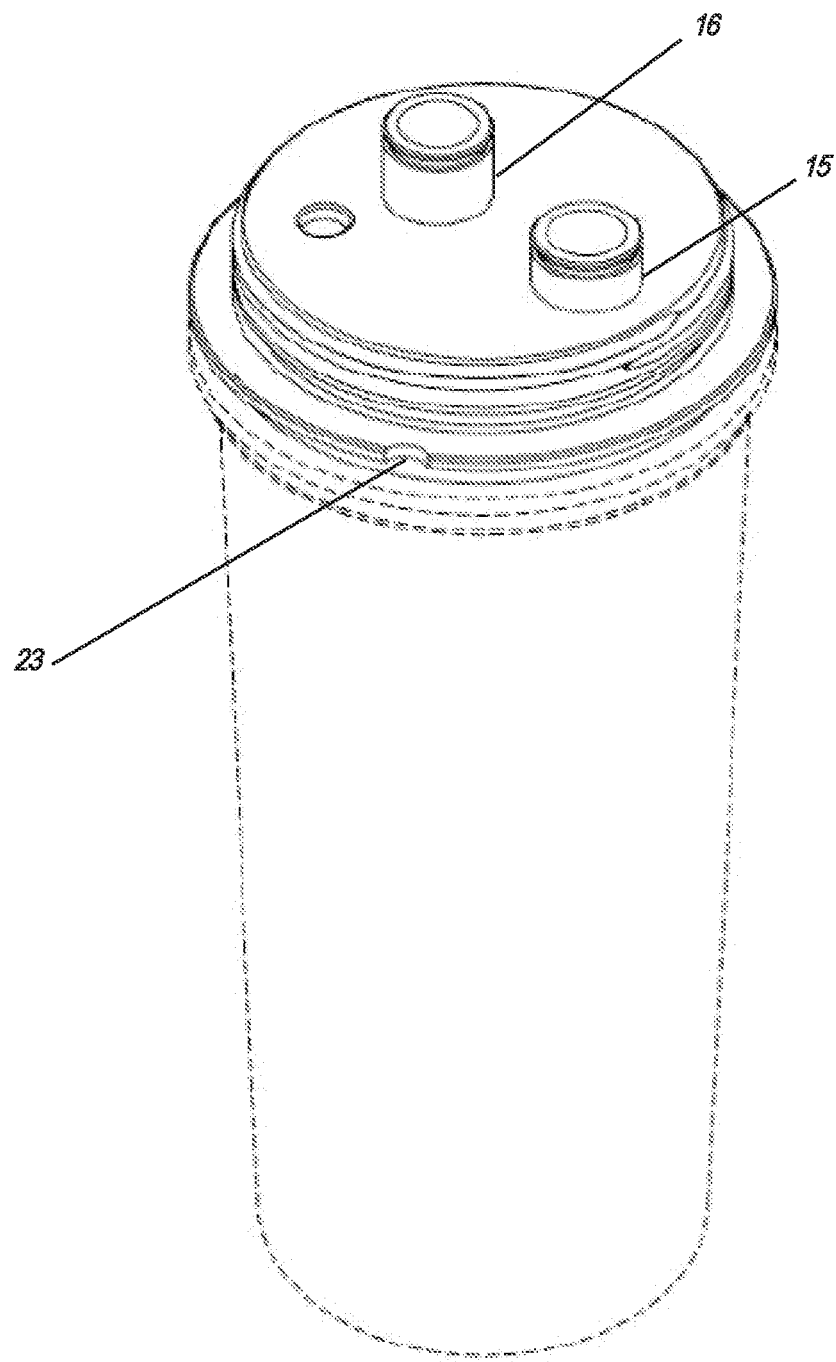
FIG. 8A is a schematic view of a third embodiment of a detachable container according to the present invention, viewing the top of the container at an angle.
Figure 8B:
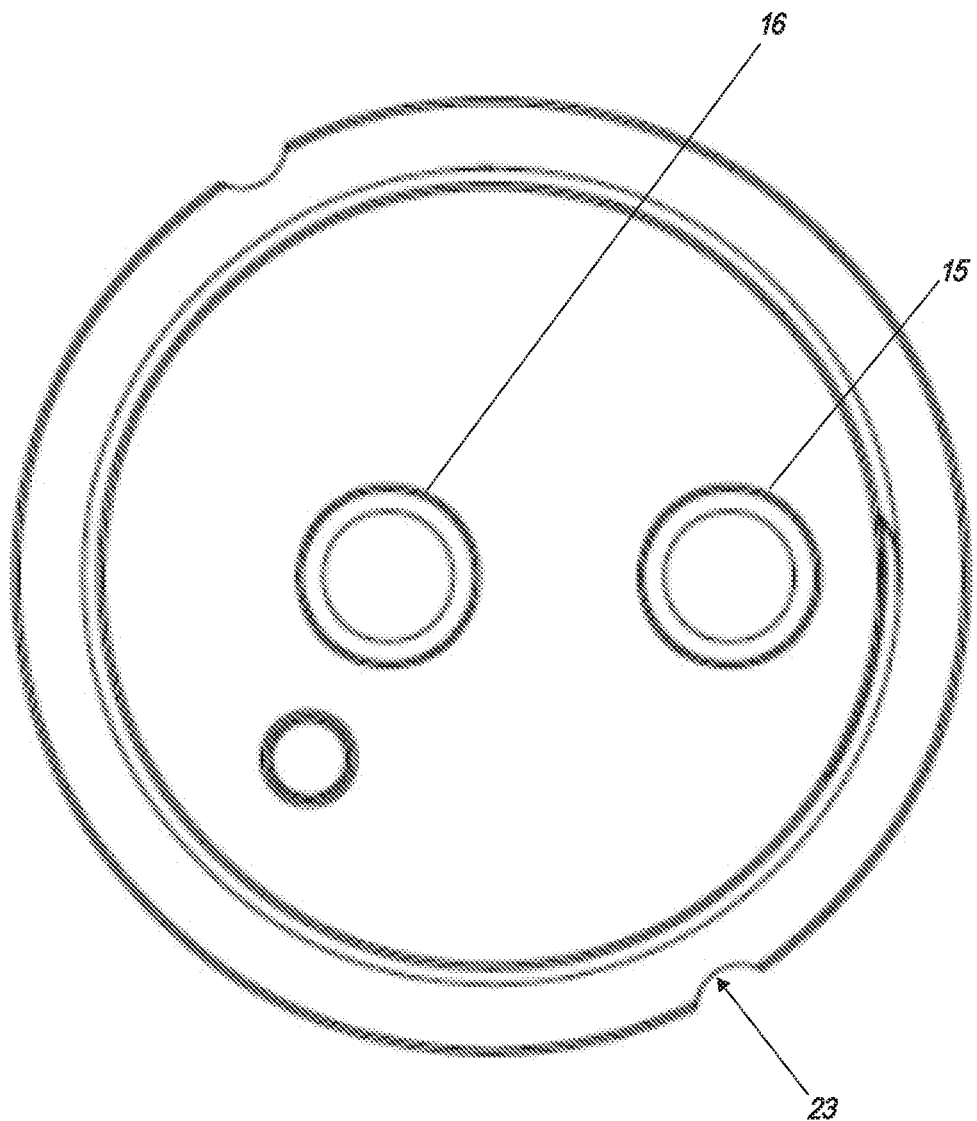
FIG. 8B is a schematic view of the same embodiment, viewing the top of the container from directly above.
Figure 9A:
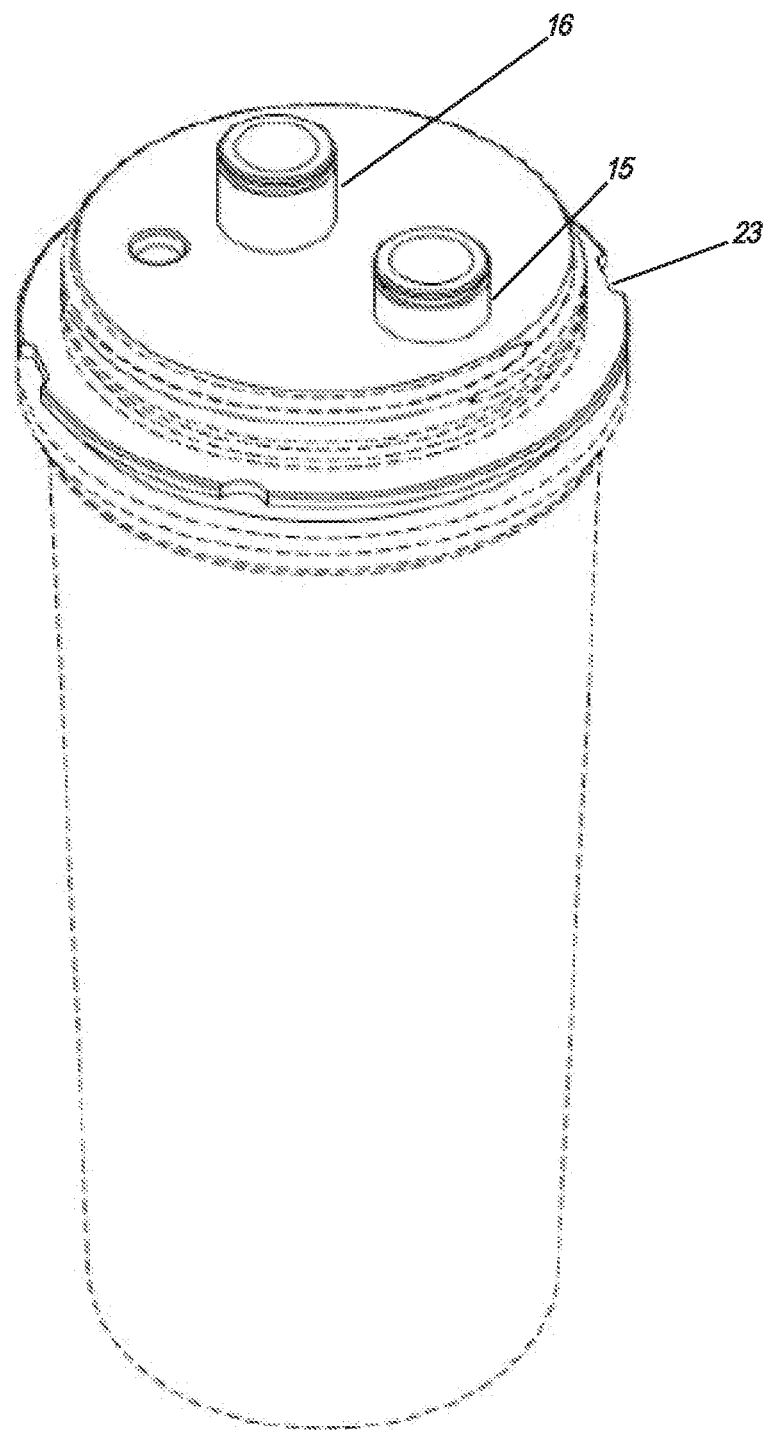
FIG. 9A is a schematic view of a fourth embodiment of a detachable container according to the present invention, viewing the top of the container at an angle.
Figure 9B:
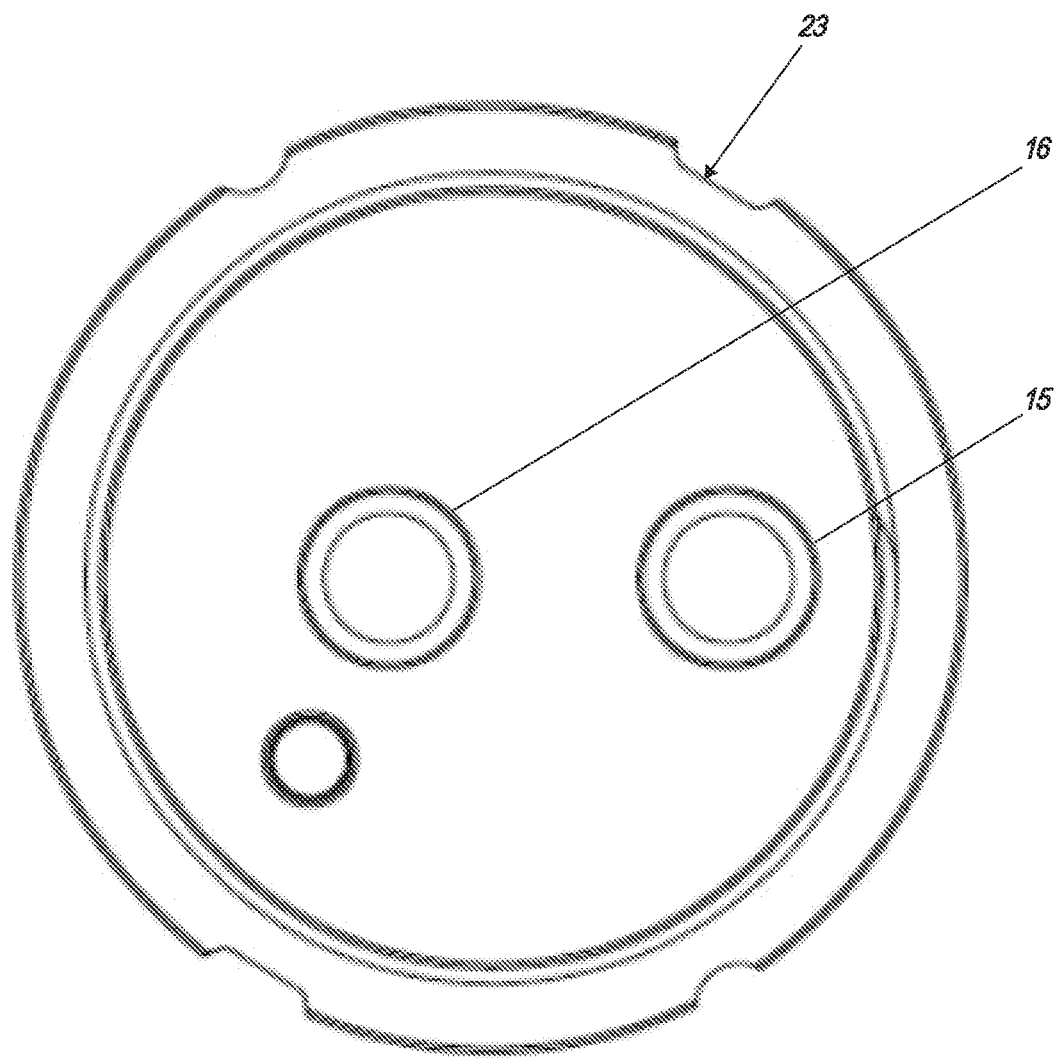
FIG. 9B is a schematic view of the same embodiment, viewing the top of the container from directly above.
Figure 10A:
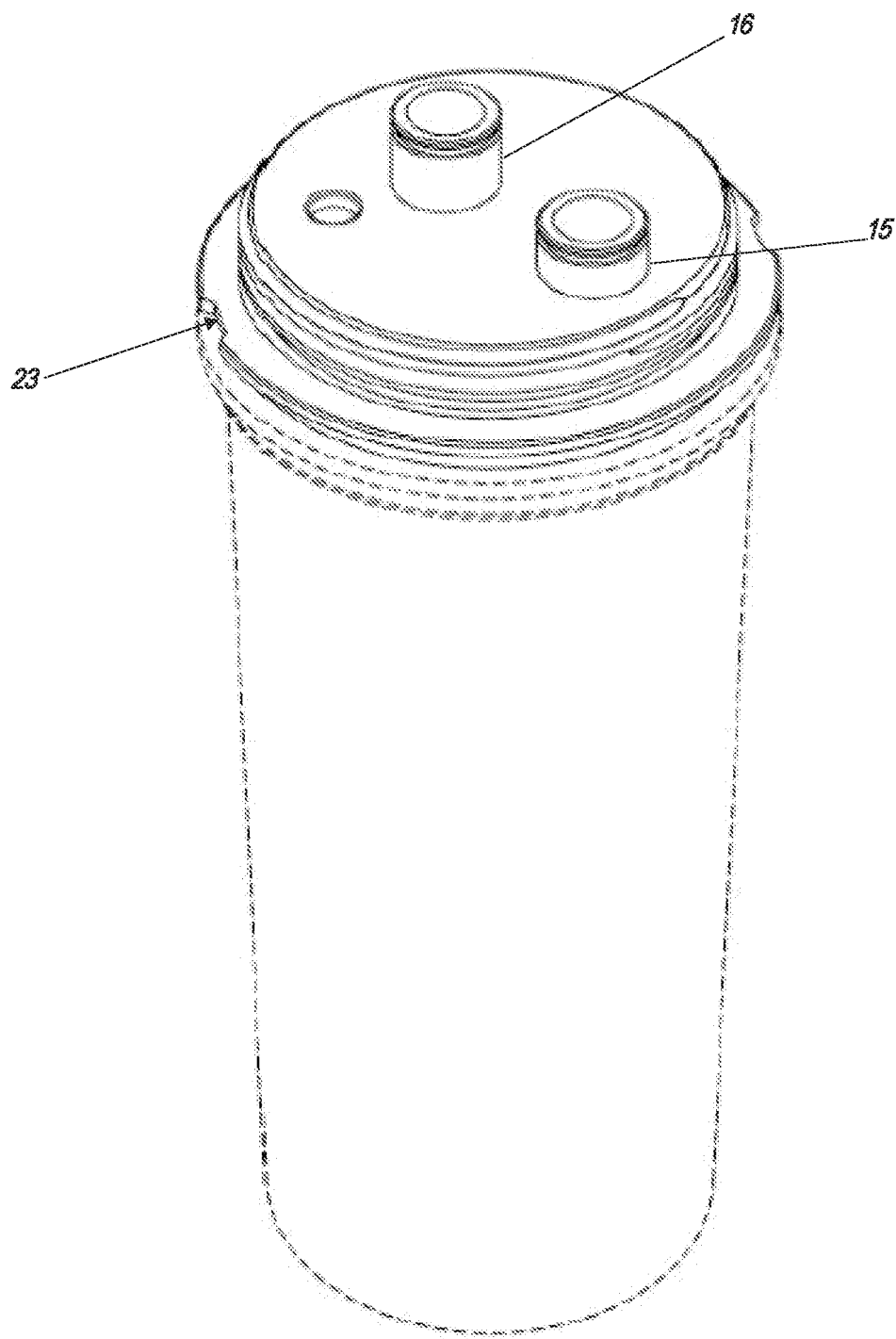
FIG. 10A is a schematic view of a fourth embodiment of a detachable container according to the present invention, viewing the top of the container at an angle.
Figure 10B:
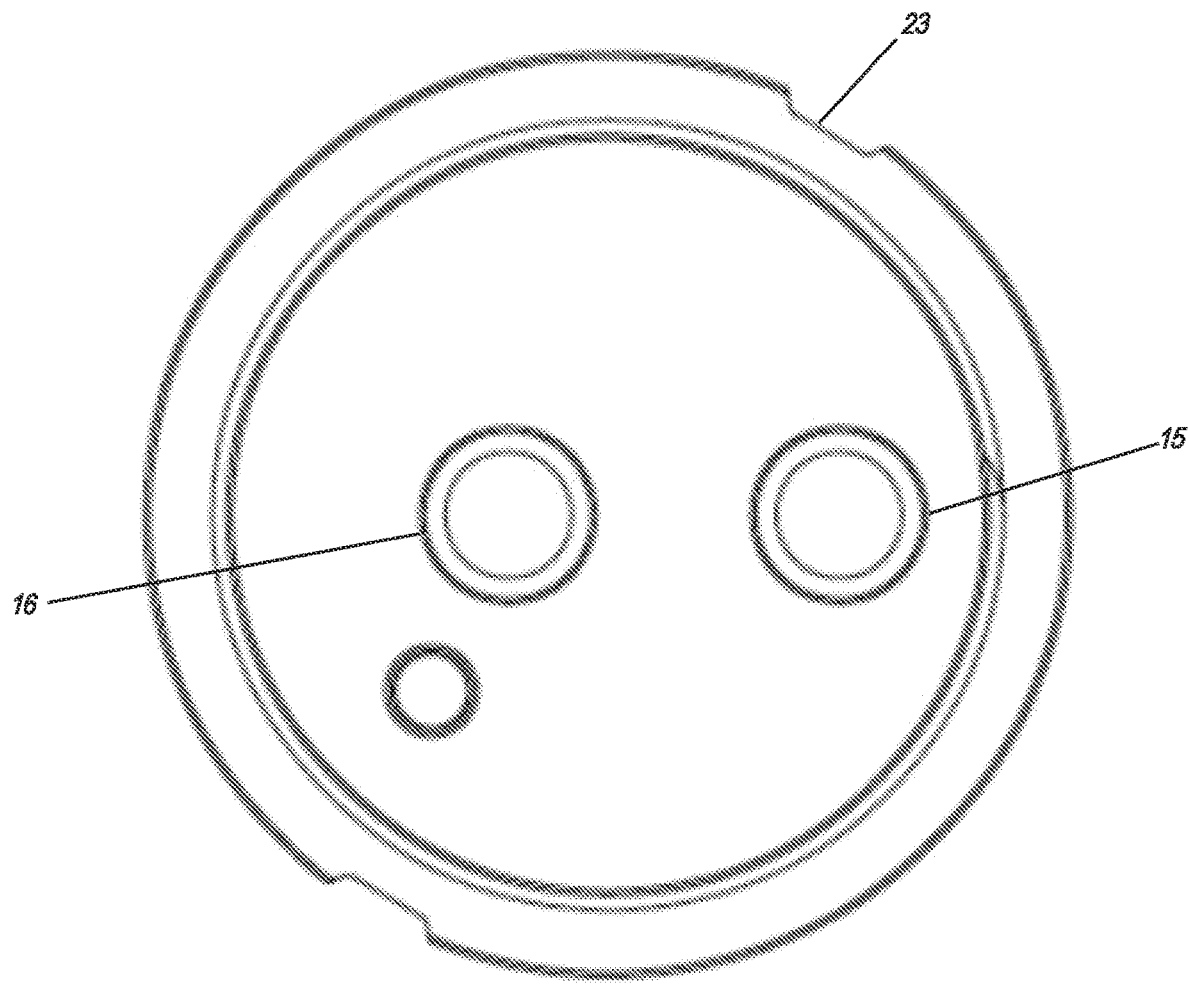
FIG. 10B is a schematic view of the same embodiment, viewing the top of the container from directly above.
Figure 11A:
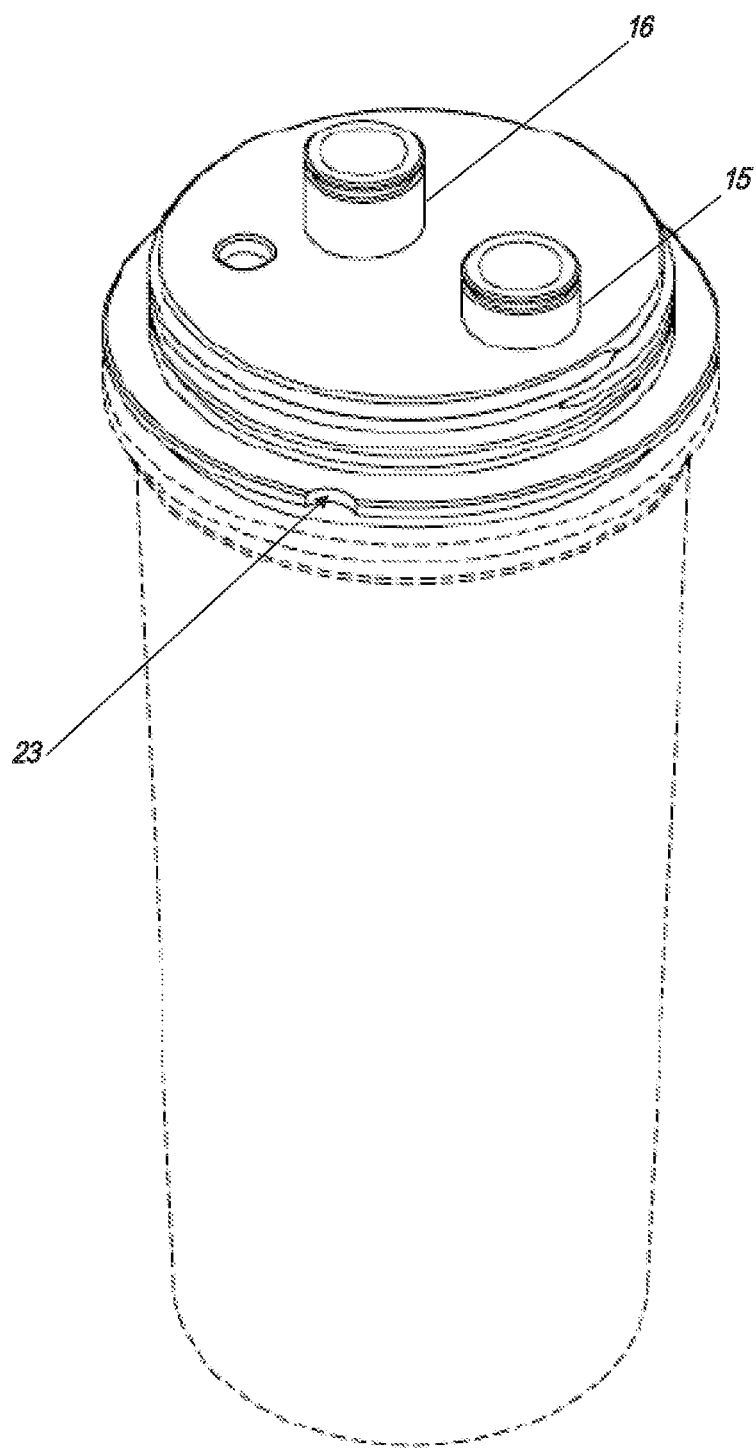
FIG. 11A is a schematic view of a fifth embodiment of a detachable container according to the present invention, viewing the top of the container at an angle.
Figure 11B:
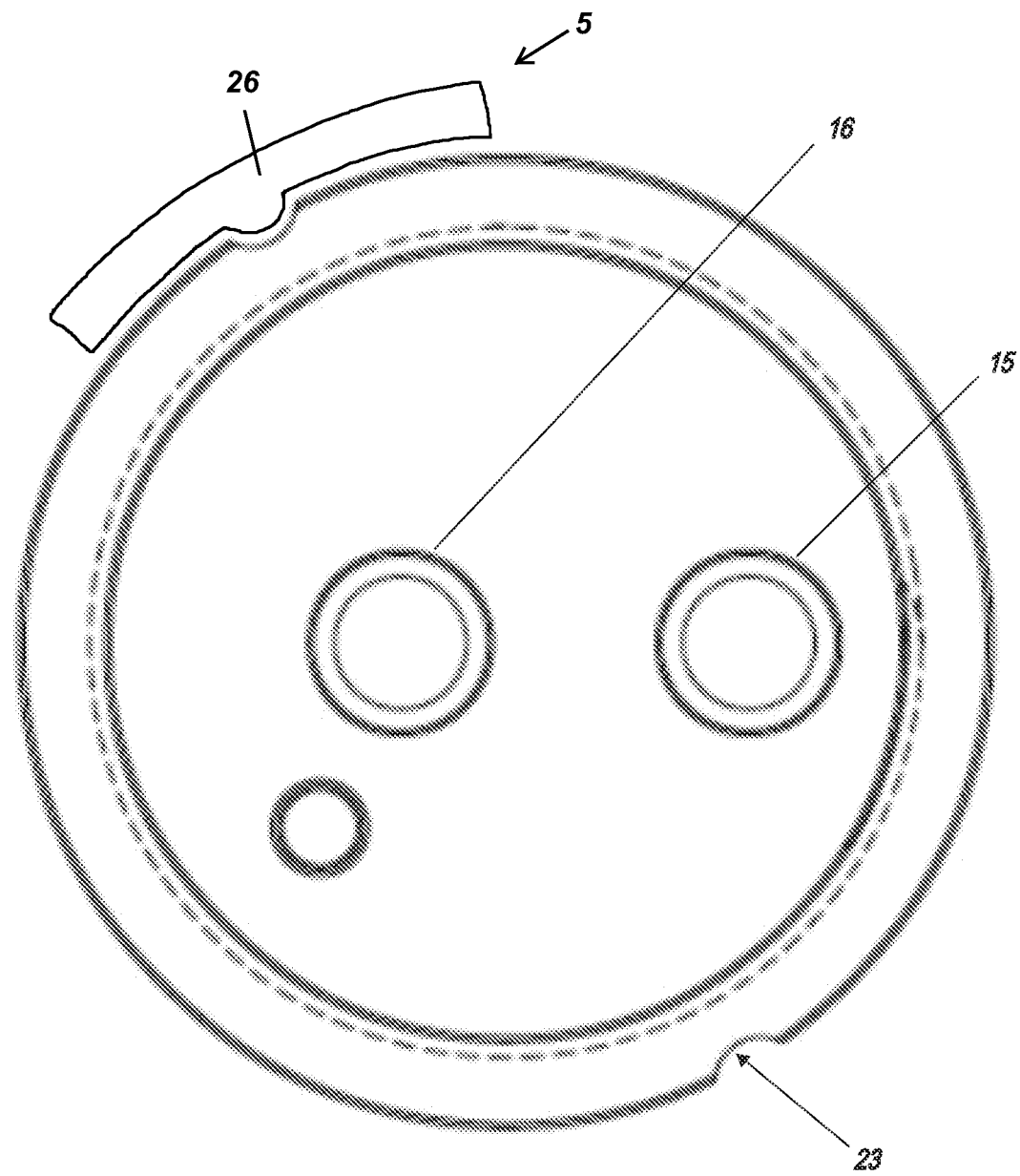
FIG. 11B is a schematic view of the same embodiment, viewing the top of the container from directly above.
Figure 12A:
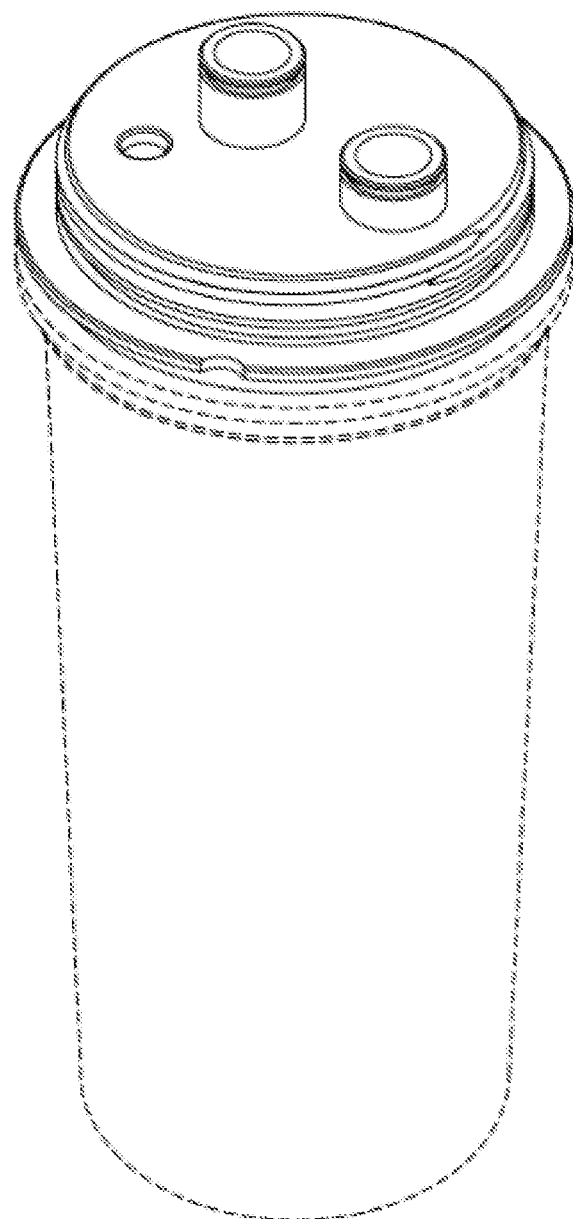
Figure 12B:
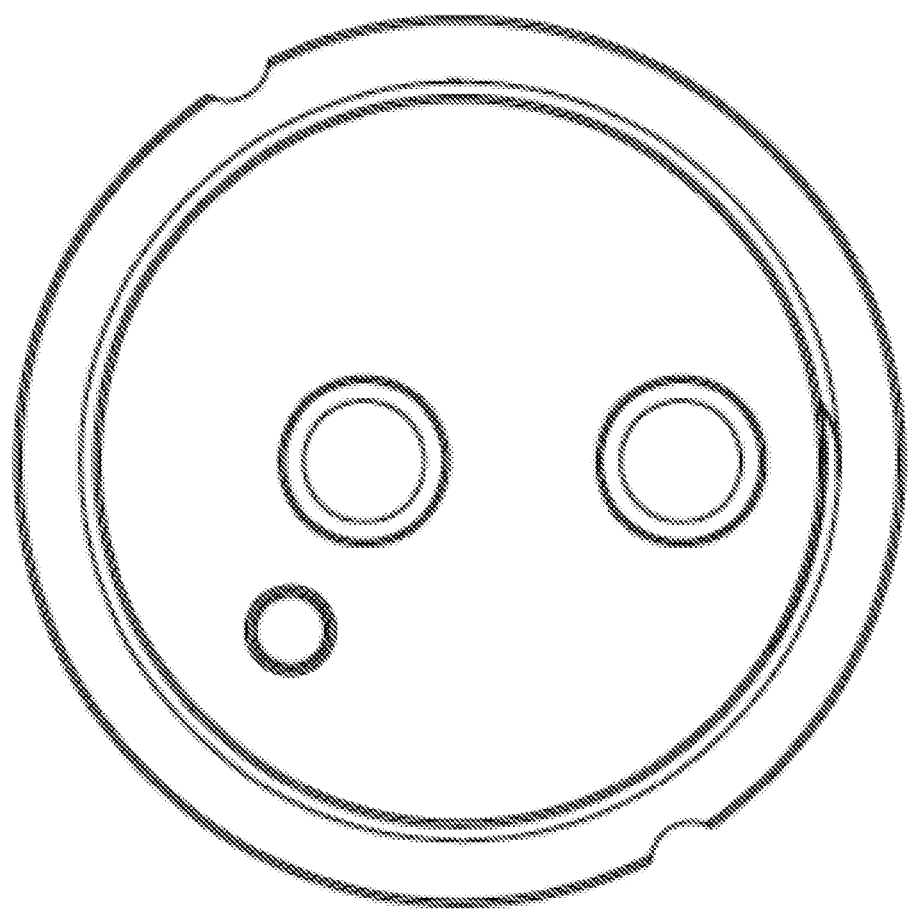
Figure 13A:
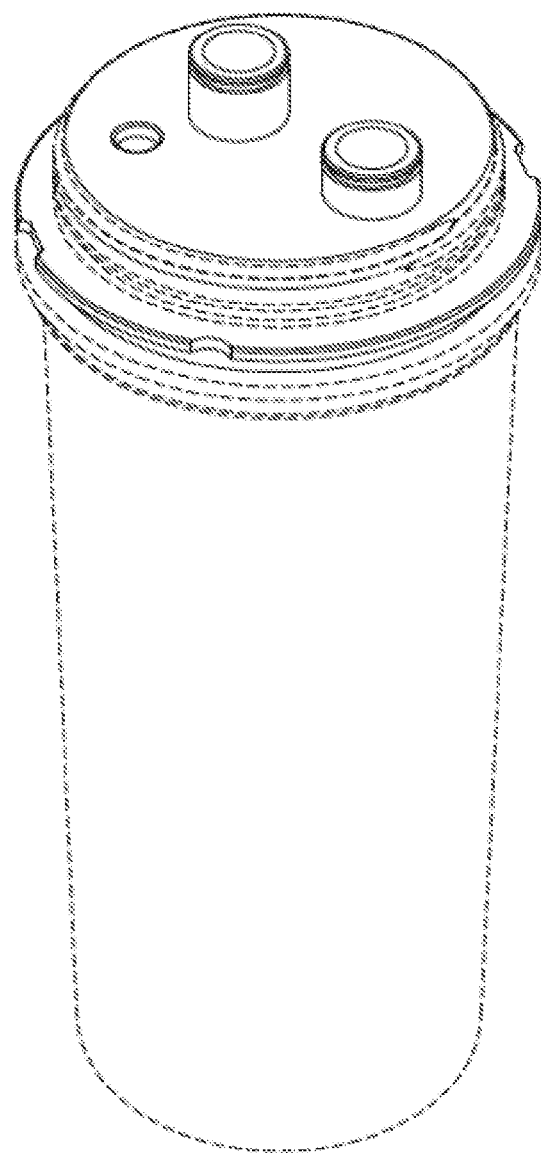
Figure 13B:
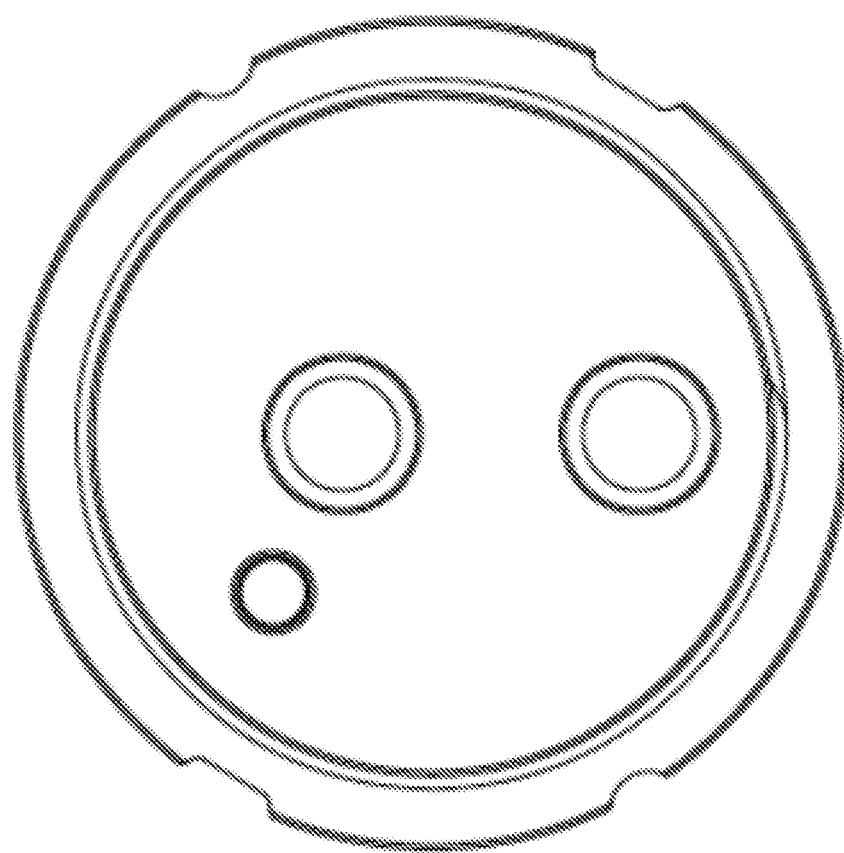
Figure 14A:
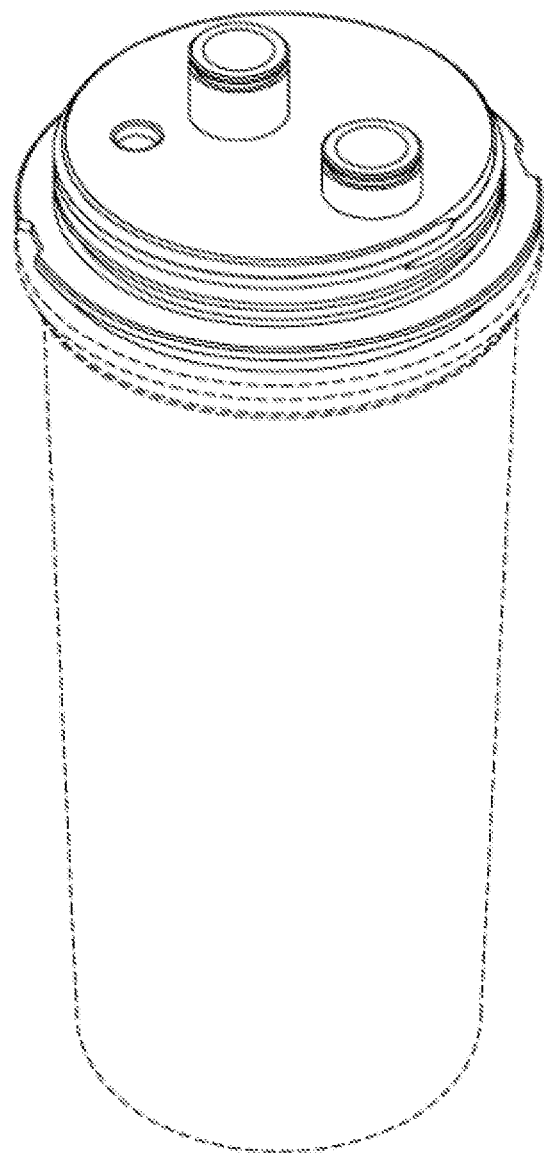
Figure 14B:
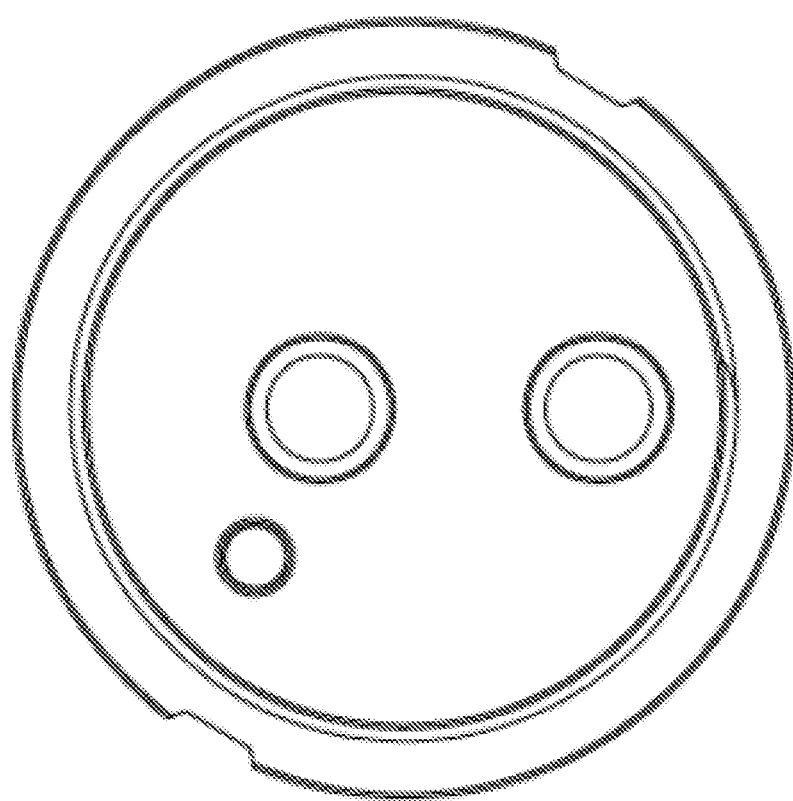
Figure 15A:
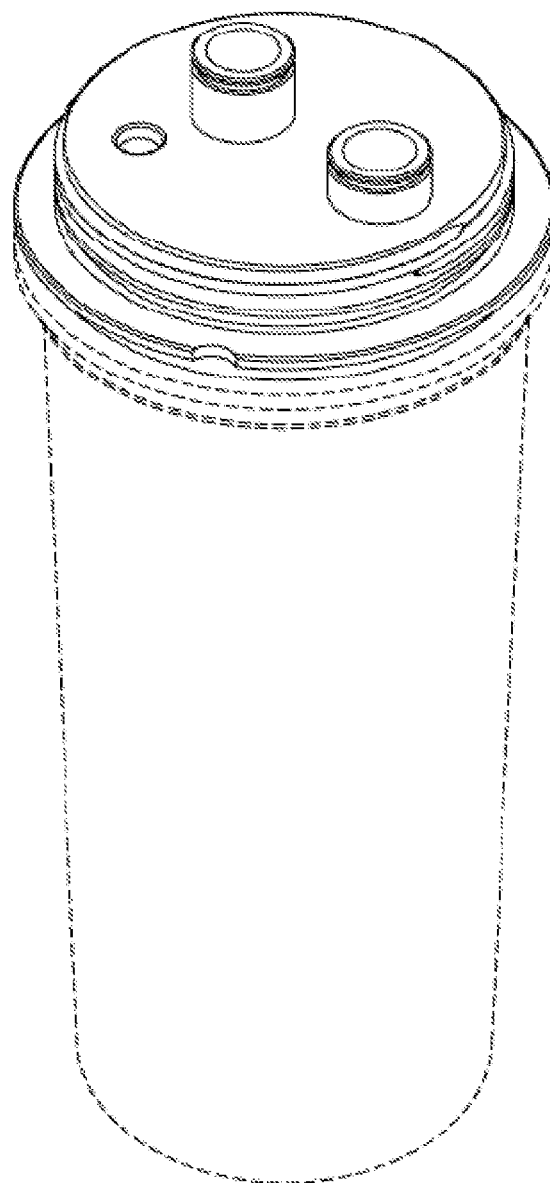
Figure 15B:
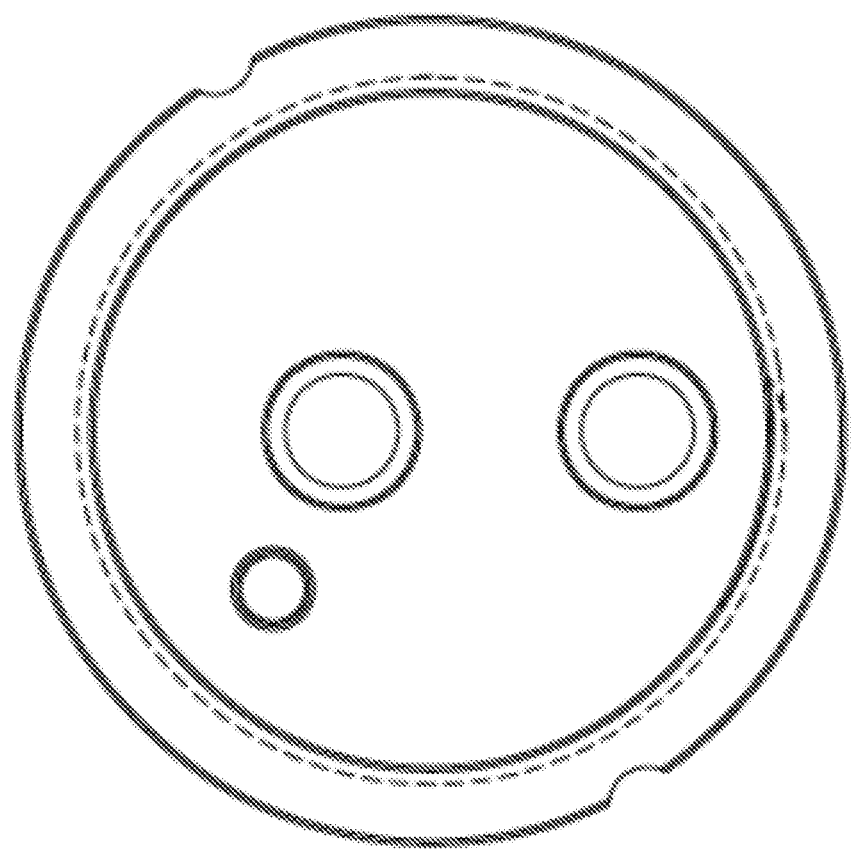

FIG. 4a shows a schematic diagram of the recycling container and cap system (see FIG. 5 for more cap 18 detail) according to the present invention. The cap 18 is a two tier shape to allow for a tight grip by both a big and smaller hand in order to achieve a strong seal as required by the invention. An O-ring 21 is provided and fits into an O-ring groove 19 on the recycling container 12 above a flange structure 22 that protrudes radially away from the central axis of the main body of the recycling container 12. The removable retaining pins 13, described above with respect to FIG. 2, fit within the region below the flange structure 22. Plugs 20 are used to provide a first leak proof seal for the recycling container 12. These plugs 20 are held in place by the cap 18 when the cap is threaded onto the recycling container as depicted in FIG. 5b.

FIG. 6 through FIG. 11 show several embodiments of irregular keyways 23 on a recycling container. The inlet port 15 and the outlet port 16 are on the circular upper surface of the container top portion, and the irregular keyways 23 are cast into the outer top mating surface for mating with a corresponding keying structure 26 (See FIG. 11B) associated with the air-water separation tank.

Generally, under present practice, the dental staff will not be able to remove deposited sediment from the recycle container nor remove accumulated particle residues from the restrictor unit themselves. Thus, it is desirable that such removal be done by a competent effluent residue processing facility. Therefore, under present practice, it is expected to be preferred that the recycling container with its enclosed restrictor unit be removed when full, or periodically replaced by fresh tanks from time to time as required. The spent tank with an accumulation of metallic and other particles can then be sent to a processing facility for proper disposal of the targeted metallic particles, such as mercury, and recovery of precious metals such as silver.

Although the sedimentary deposit process is effective to remove a satisfactorily high proportion of the target particles desired to be removed from the effluent, the recycling container desirably includes an outlet restrictor right in the chamber to catch any floating materials as well as any other materials that did not settle out.

If the recycle container is not changed as required or filled beyond normal capacity, waste liquid from dental practice may back up into air water separator tank. Should this occur, effluent overflows through the air suction tube and into the outlet port and is discharged into the vacuum pump draw line and thence eventually into the municipal drain. However, it is desirable that the system should operate in such a manner as to avoid having the air-water separator tank become completely full, since effluent exiting through the air outlet port will contain particles that will not be separated by the separator. If, however, such a by-pass condition occurs at no time will the suction generated by the vacuum pump be lost or interrupted at the dental office.

In a further embodiment of the invention oriented towards large-scale institutional applications, in which many dental chairs or other sources of effluent are connected to the same suction and drain services, several parallel-connected recycling containers and associated apparatus, each such composite apparatus including a air-water separator tank and preferably one, or alternatively two attached recycling containers, may be operated in parallel to provide sufficient treatment capacity for large effluent volumes.

All publications, web-sites, patents and patent applications cited in the specification are hereby incorporated herein by reference in their entirety for the disclosure for which they are cited.

Having read the above specification, other alternatives and variants of the above described methods and apparatus suitable for practicing the methods will occur to those skilled in the technology. Such alternatives, modifications and variants fall within the scope of the present invention.

The invention as described above also includes the following non-limiting claims, which describe particular embodiments of the invention.

The invention claimed is:

1. A detachable dental-amalgam container for use with a dental amalgam separation system, the dental amalgam separation system having a vacuum source that applies a pressure within the dental amalgam separation system to cause movement of dental amalgam effluent within the detachable dental-amalgam container, the dental amalgam separation system having at least one retaining pin for use with the detachable dental-amalgam container, the detachable dental-amalgam container comprising:
   a main body having an interior volume for receiving the dental amalgam effluent from the dental amalgam separation system;
   a container top portion located at a top of the main body, the container top portion including a generally cylindrical upper region having a circular upper surface from which a container inlet port and a container outlet port extend away from the main body, the container inlet port being positioned nearer to a periphery of the circular upper surface than the container outlet port, the container inlet port for receiving the dental amalgam effluent from the dental amalgam separation system, the container top portion further including at least one radially protruding structure located below the generally cylindrical upper region, the at least one radially protruding structure for engaging the at least one retaining pin of the dental amalgam separation system to ensure the detachable dental-amalgam container does not become detached from the dental amalgam separation system when the pressure is released from the vacuum source, the at least one radially protruding structure being located radially outward relative to the periphery of the circular upper surface.

2. The detachable dental-amalgam container of claim 1, further including a container inlet conduit extending downwardly from the container top portion and into the interior volume, the container inlet conduit being fluidically coupled to the container inlet port, the container inlet conduit and the container inlet port for transferring the dental amalgam effluent from the dental amalgam separation system to the interior volume of the main body.

3. The detachable dental-amalgam container of claim 1, wherein the inlet port and the outlet port are of the same height.

4. The detachable dental-amalgam container of claim 1, wherein the container top portion has a maximum outer dimension that is greater than a maximum outer diameter of the main body.

5. The detachable dental-amalgam container of claim 1, further including a pair of plugs configured to seal a container inlet port and a container outlet port of a filled detachable dental-amalgam container.

6. The detachable dental-amalgam container of claim 5, further including a cap configured to retain at least one of the plugs on the filled detachable dental-amalgam container.

7. The detachable dental-amalgam container of claim 6, wherein the cap mates with threads on the generally cylindrical upper region to hold the pair of plugs in place.

8. The detachable dental-amalgam container of claim 1, wherein the at least one radially protruding structure defines a maximum outer dimension for the container top portion.

9. The detachable dental-amalgam container of claim 1, wherein the generally cylindrical upper region includes external threads.

10. The detachable dental-amalgam container of claim 1, wherein the at least one radially protruding structure includes a flange structure extending in a direction away from the generally cylindrical upper region.

11. The detachable dental-amalgam container of claim 10, wherein the flange structure extends entirely around the container top portion.

12. The detachable dental-amalgam container of claim 10, wherein the flange structure includes a curved outer surface.

13. A detachable dental-amalgam container for use with a dental amalgam separation system, the dental amalgam separation system having a tank that holds dental amalgam effluent and at least one retaining pin for use with the detachable dental-amalgam container, the detachable dental-amalgam container comprising:
   a main body having an interior volume for receiving the dental amalgam effluent from the tank of the dental amalgam separation system;
   a container top portion located at a top of the main body, the container top portion including a generally cylindrical upper region having an upper surface from which a container inlet port and a container outlet port extend away from the main body, the container inlet port being positioned nearer to a periphery of the upper surface than the container outlet port, each of the container inlet port and the container outlet port is configured to help provide a seal between the detachable dental-amalgam container and the dental amalgam separation system, the container top portion further including at least one radially protruding structure located below the generally cylindrical upper region, the at least one retaining pin of the dental amalgam separation system adapted to be received below the at least one radially protruding structure to ensure the detachable dental-amalgam container does not become detached from the dental amalgam separation system, the at least one radially protruding structure protrudes radially outward of the container top portion such that it is located outward from the periphery of the upper surface;
   a container inlet conduit extending downwardly from the container top portion and into the interior volume, the container inlet conduit being coupled to the container inlet port, the container inlet conduit and the container inlet port for transferring the dental amalgam effluent from the tank of the dental amalgam separation system to the interior volume of the main body; and
   wherein the container outlet port is for being coupled to a system outlet port of the dental amalgam separation system such that the fluid from the dental amalgam effluent is moved from the interior volume of main body, through the container outlet port, and into the system outlet.

14. The detachable dental-amalgam container of claim 13, further including a pair of plugs configured to seal a container inlet port and a container outlet port of a filled detachable dental-amalgam container, and a cap that retains at least one of the plugs on the filled detachable dental-amalgam container.

15. The detachable dental-amalgam container of claim 13, wherein the at least one radially protruding structure includes a flange structure extending away from a lower portion of the generally cylindrical upper region.

16. The detachable dental-amalgam container of claim 15, wherein the flange structure extends entirely around the container top portion.

17. The detachable dental-amalgam container of claim 15, wherein the flange structure includes a curved outer surface.

18. The detachable dental-amalgam container of claim 13, wherein the generally cylindrical upper region includes external threads.

19. The detachable dental-amalgam container of claim 13, further including a restrictor located within the interior volume of the main body and fluidically coupled to the container outlet port, the restrictor configured to remove fine particles from the dental amalgam effluent so that the fine particles are not discharged from the container outlet port.

20. A detachable dental-amalgam container for use with a dental amalgam separation system, the dental amalgam separation system having a tank for receiving the dental amalgam effluent and at least one retaining pin for use with the detachable dental-amalgam container, the detachable dental-amalgam container comprising:
- a main body having an interior volume for receiving the dental amalgam effluent from the tank of the dental amalgam separation system;
- a container top portion located at a top of the main body, the container top portion including a generally cylindrical upper region having a circular upper surface from which a container inlet port and a container outlet port extend away from the main body, the container inlet port being positioned nearer to a periphery of the circular upper surface than the container outlet port, the container inlet port for receiving the dental amalgam effluent from the tank of the dental amalgam separation system, the container top portion further including at least one radially protruding structure located below the generally cylindrical upper region, the at least one radially protruding structure being located radially outward relative to the periphery of the circular upper surface, the at least one radially protruding structure for being positioned above the at least one retaining pin of the dental amalgam separation system to ensure the detachable dental-amalgam container does not become detached from the dental amalgam separation system.

21. The detachable dental-amalgam container of claim 20, further including a restrictor located within the interior volume of the main body and fluidically coupled to the container outlet port, the restrictor configured to remove fine particles from the dental amalgam effluent so that the fine particles are not discharged from the container outlet port.

* * * * *